US007989613B2

(12) United States Patent
Shaw et al.

(10) Patent No.: US 7,989,613 B2
(45) Date of Patent: Aug. 2, 2011

(54) INHIBITION OF METALLO-β-LACTAMASE BY RNA

(75) Inventors: Robert W. Shaw, Lubbock, TX (US); Kyu Mee Kim, Lubbock, TX (US)

(73) Assignee: Texas Tech University, Lubbock, TX (US)

( * ) Notice: Subject to any disclaimer, the term of this patent is extended or adjusted under 35 U.S.C. 154(b) by 0 days.

(21) Appl. No.: 11/663,713

(22) PCT Filed: Oct. 19, 2005

(86) PCT No.: PCT/US2005/037706
§ 371 (c)(1), (2), (4) Date: Mar. 23, 2007

(87) PCT Pub. No.: WO2006/135431
PCT Pub. Date: Dec. 21, 2006

(65) Prior Publication Data
US 2008/0119432 A1 May 22, 2008

(51) Int. Cl.
*C07H 21/02* (2006.01)
*C07H 21/04* (2006.01)

(52) U.S. Cl. ..................... 536/24.5; 536/23.1; 536/24.3; 536/24.33

(58) Field of Classification Search ........................ None
See application file for complete search history.

(56) References Cited

U.S. PATENT DOCUMENTS 5,637,459 A 6/1997 Burke et al.
5,773,598 A 6/1998 Burke et al.

FOREIGN PATENT DOCUMENTS

WO WO 2004/031142 A2 4/2004

OTHER PUBLICATIONS

Shaw RW. et al. (1991) "Hyperexpression in *Escherichia coli*, purification, and characterization of the metallo-beta-lactamase of *Bacillus cereus* 5/B/6" Protein Expr Purif. Apr.-Jun.;2(2-3):151-7.*
Shaw et al. (Mar. 2003) "Inhibition of bacterial metallo-beta-lactamase" FASEB J. vol. 17, No. 4-5, pp. Abstract No. 623.6.*
Burgess et al. (1990) J. of Cell Bio. 111:2129-2138.*
Lazar et al. (1988) Molecular and Cellular Biology 8:1247-1252.*
Jen et al. (2000) Stem Cells 18:307-319.*
Lim et al. (1988) "Cloning, nucleotide sequence, and expression of the *Bacillus cereus* 5/B/6 beta-lactamase II structural gene" J. Bacteriol. 170, 2873-2878.*
Abraham EP, Waley SG. Beta-Lactamases from *Bacillus cereus*. Academic Press, New York. 1979:311-338.
Alberts IL, Nadassy K, Wodak SJ. Analysis of zinc binding sites in protein crystal structures. Protein Sci. Aug. 1998;7(8):1700-16.
Ambler RP. The structure of beta-lactamases. Philos Trans R Soc Lond B Biol Sci. May 16, 1980;289(1036):321-31.

(Continued)

*Primary Examiner* — Sean McGarry
*Assistant Examiner* — Terra Cotta Gibbs
(74) *Attorney, Agent, or Firm* — Roman Aguilera

(57) ABSTRACT

Compositions and methods for identifying polyribonucleotides that binds with high affinity to a metallo-β-lactamase. The polyribonucleotides inhibit the activity of the metallo-β-lactamase.

4 Claims, 19 Drawing Sheets

Penicillins

Cephalosporins

OTHER PUBLICATIONS

Aptamera. Lead Anti-Cancer Druig Compound—AGRO 100. http://www.aptamera.com/aptamers_leaddrugcandidate.pdf. 2004.
Bartel DP, Szostak JW. Isolation of new ribozymes from a large pool of random sequences. Science. Sep. 10, 1993;261(5127):1411-8.
Bassett SE, Fennewald SM, King DJ, Li X, Herzog NK, Shope R, Aronson JF, Luxon BA, Gorenstein DG. Combinatorial selection and edited combinatorial selection of phosphorothioate aptamers targeting human nuclear factor-kappaB RelA/p50 and RelA/RelA. Biochemistry. Jul. 20, 2004;43(28):9105-15.
Bicknell R, Schaffer A, Waley SG, Auld DS. Changes in the coordination geometry of the active-site metal during catalysis of benzylpenicillin hydrolysis by *Bacillus cereus* beta-lactamase II. Biochemistry. Nov. 4, 1986;25(22):7208-15.
Bounaga S, Laws AP, Galleni M, Page MI. The mechanism of catalysis and the inhibition of the *Bacillus cereus* zinc-dependent beta-lactamase. Biochem J. May 1, 1998;331 ( Pt 3):703-11.
Brenner DG, Knowles JR. Penicillanic acid sulfone: nature of irreversible inactivation of RTEM beta-lactamase from *Escherichia coli*. Biochemistry. Nov. 20, 1984;23(24):5833-9.
Carfi A, Pares S, Duee E, Galleni M, Duez C, Frere JM, Dideberg O. The 3-D structure of a zinc metallo-beta-lactamase from *Bacillus cereus* reveals a new type of protein fold. EMBO J. Oct. 16, 1995;14(20):4914-21.
Concha NO, Janson CA, Bowling P, Pearson S, Cheever CA, Clarke BP, Lewis C, Galleni M, Frere JM, Payne DJ, Bateson JH, Abdel-Meguid SS. Crystal structure of the IMP-1 metallo beta-lactamase from *Pseudomonas aeruginosa* and its complex with a mercaptocarboxylate inhibitor: binding determinants of a potent, broad-spectrum inhibitor. Biochemistry. Apr. 18, 2000;39(15):4288-98.
Concha NO, Rasmussen BA, Bush K, Herzberg O. Crystal structure of the wide-spectrum binuclear zinc beta-lactamase from *Bacteroides fragilis*. Structure. Jul. 15, 1996;4(7):823-36.
Crompton B, Jago M, Crawford K, Newton GG, Abraham EP. Behaviour of some derivatives of 7-aminocephalosporanic acid and 6-aminopenicillanic acidas substrates, inhibitors and inducers of penicillinases. Biochem J. Apr. 1962;83:52-63.
Danziger LH, Pendland SL. Bacterial resistance to beta-lactam antibiotics. Am J Health Syst Pharm. Mar. 15, 1995;52(6 Suppl 2):S3-8.
Davies RB, Abraham, EP, Fleming J, P Comparison of beta-lactamase II from *Bacillus cereus* 569/H/9 with a beta-lactamase from *Bacillus cereus* 5/B/6.ollock MR. Biochem J. Feb. 1975;145(2):409-11.
Davies RB, Abraham EP. Metal cofactor requirements of beta-lactamase II. Biochem J. Oct. 1974;143(1):129-35.
Davies RB, Abraham EP. Separation, purification and properties of beta-lactamase I and beta-lactamase II from *Bacillus cereus* 569/H/9. Biochem J. Oct. 1974;143(1):115-27.
Eyetech Pharmaceuticals. Macugen-Basics. http://www.eyetk.com/science/science_vegf.asp. 2004.
Felici A, Amicosante G, Oratore A, Strom R, Ledent P, Joris B, Fanuel L, Frere JM. An overview of the kinetic parameters of class B beta-lactamases. Biochem J. Apr. 1, 1993;291 ( Pt 1):151-5.
Fisher J, Charnas RL, Bradley SM, Knowles JR. Inactivation of the RTEM beta-lactamase from *Escherichia coli*. Interaction of penam sulfones with enzyme. Biochemistry. May 12, 1981;20(10):2726-31.
Fitzgerald PM, Wu JK, Toney JH. Unanticipated inhibition of the metallo-beta-lactamase from Bacteroides fragilis by 4-morpholineethanesulfonic acid (MES): a crystallographic study at 1.85-A resolution. Biochemistry. May 12, 1998;37(19):6791-800.
Folk JE, Schirmer EW. The Porcine Pancreatic Carboxypeptidase A System. I. Three Forms of the Active Enzyme. J Biol Chem. Dec. 1963:238:3884-94.
Freier SM, Kierzek R, Jaeger JA, Sugimoto N, Caruthers MH, Neilson T, Turner DH. Improved free-energy parameters for predictions of RNA duplex stability. Proc Natl Acad Sci U S A. Dec. 1986;83(24):9373-7.
Frere JM. Beta-lactamases and bacterial resistance to antibiotics. Mol Microbiol. May 1995;16(3):385-95.
Garcia-Saez I, Hopkins J, Papamicael C, Franceschini N, Amicosante G, Rossolini GM, Galleni M, Frere JM, Dideberg O. The 1.5-A structure of Chryseobacterium meningosepticum zinc beta-lactamase in complex with the inhibitor, D-captopril. J Biot Chem. Jul. 27, 2003;278(26):23868-73. Epub Apr. 8, 2003.
Gold L, Polisky B, Uhlenbeck O, Yarus M. Diversity of oligonucleotide functions. Annu Rev Biochem. 1995;64:763-97.
Hanahan D. Studies on transformation of *Escherichia coli* with plasmids. J Mol Biol. Jun. 5, 1983;166(4):557-80.
Hussain M, Pastor FI, Lampen JO. Cloning and sequencing of the blaZ gene encoding beta-lactamase III, a lipoprotein of *Bacillus cereus* 569/H. J Bacteriol. Feb. 1987;169(2):579-86.
Jaeger JA, Turner DH, Zuker M. Improved predictions of secondary structures for RNA. Proc Natl Acad Sci U S A. Oct. 1989;86(20):7706-10.
Jaeger JA, Turner DH, Zuker M. Predicting optimal and suboptimal secondary structure for RNA. Methods Enzymol. 1990;183:281-306.
Joris B, Ledent P, Dideberg O, Fonze E, Lamotte-Brasseur J, Kelly JA, Ghuysen JM, Frere JM. Comparison of the sequences of class A beta-lactamases and of the secondary structure elements of penicillin-recognizing proteins. Antimicrob Agents Chemother. Nov. 1991;35(11):2294-301.
Kelly JA, Knox JR, Moews PC, Moring J, Zhao HC. Molecular Graphics: Studying Beta-Lactam Inhibition in Three Dimensions. American Society for Microbiology, Washington, D.c. 1998:261-267.
Klug SJ, Famulok M. All you wanted to know about SELEX. Mol Biol Rep. 1994;20(2):97-107.
Kuwabara S, Lloyd PH. Protein and carbohydrate moieties of a preparation of -lactamase II. Biochem J. Aug. 1971;124(1):215-20.
Ledent P, Raquet X, Joris B, Van Beeumen J, Frere JM. A comparative study of class-D beta-lactamases. Biochem J. Jun. 1, 1993;292 ( Pt 2):555-62.
Lim HM, Pene JJ, Shaw RW. Cloning, nucleotide sequence, and expression of the *Bacillus cereus* 5/B/6 beta-lactamase II structural gene. J Bacteriol. Jun. 1988;170(6):2873-8.
Livermore DM. Mechanisms of resistance to beta-lactam antibiotics. Scand J Infect Dis Suppl. 1991;78:7-16.
Lowry OH, Rosebrough NJ, Farr AL, Randall RJ. Protein measurement with the Folin phenol reagent. J Biol Chem. Nov. 1951;193(1):265-75.
Maugh TH. A new wave of antibiotics builds. Science. Dec. 11, 1981;214(4526):1225-8.
Maxam AM, Gilbert W. A new method for sequencing DNA. Proc Natl Acad Sci U S A. Feb. 1977;74(2):560-4.
Myers JL, Shaw RW. Production, purification and spectral properties of metal-dependent beta-lactamases of *Bacillus cereus*. Biochim Biophys Acta. May 1, 1989;995(3):264-72.
Mollard C, Moali C, Papamicael C, Damblon C, Vessilier S, Amicosante G, Schofield CJ, Galleni M, Frere JM, Roberts GC. Thiomandelic acid, a broad spectrum inhibitor of zinc beta-lactamases: kinetic and spectroscopic studies. J Biol Chem. Nov. 30, 2001;276(48):45015-23. Epub Sep. 19, 2001.
NEU HC. The crisis in antibiotic resistance. Science. Aug. 21, 1992;257(5073):1064-73.
Novartis Ophthalmics. Vitravene. http://www.isispharm.com/vitravene-P.html. 2004.
Payne DJ, Bateson JH, Gasson BC, Proctor D, Khushi T, Farmer TH, Tolson DA, Bell D, Skett PW, Marshall AC, Reid R, Ghosez L, Combret Y, Marchand-Brynaert J. Inhibition of metallo-beta-lactamases by a series of mercaptoacetic acid thiol ester derivatives. Antimicrob Agents Chemother. Jan. 1997;41(1):135-40.
Payne DJ, Hueso-Rodriguez JA, Boyd H, Concha NO, Janson CA, Gilpin M, Bateson H, Cheever C, Niconovich NL, Pearson S, Rittenhouse S, Tew D, Diez E, Perez P, De La Fuente J, Rees M, Rivera-Sagredo A. Identification of a series of tricyclic natural products as potent broad-spectrum inhibitors of metallo-beta-lactamases. Antimicrob Agents Chemother. Jun. 2002;46(6):1880-6.
Pitout JD, Sanders CC, Sanders WE Jr. Antimicrobial resistance with focus on beta-lactam resistance in gram-negative bacilli. Am J Med. Jul. 1997;103(1):51-9. (Abstract Only).
Rahil J, Pratt RF. Phosphonate monoester inhibitors of class A beta-lactamases. Biochem J. May 1, 1991;275 ( Pt 3):793-5.

Rasmussen BA, Yang Y, Jacobus N, Bush K. Contribution of enzymatic properties, cell permeability, and enzyme expression to microbiological activities of beta-lactams in three Bacteroides fragilis isolates that harbor a metallo-beta-lactamase gene. Antimicrob Agents Chemother. Sep. 1994:38(9):2116-20.
Reddy P, Peterkofsky A, McKenney K. Hyperexpression and purification of *Escherichia coli* adenylate cyclase using a vector designed for expression of lethal gene products. Nucleic Acids Res. Dec. 25, 1989;17(24):10473-88.
Robertson DL, Joyce GF. Selection in vitro of an RNA enzyme that specifically cleaves single-stranded DNA. Nature. Mar. 29, 1990;344(6265):467-8.
Sambrook J, Fritsch EF, Maniatis T. Molecular Cloning: A Laboratory Manual. Cold Spring Harbor Laboratory Press, New York. 1989. 2ed:7.70-7.76.
Scrofani SD, Chung J, Huntley JJ, Benkovic SJ, Wright PE, Dyson HJ. NMR characterization of the metallo-beta-lactamase from Bacteroides fragilis and its interaction with a tight-binding inhibitor: role of an active-site loop. Biochemistry. Nov. 2, 1999;38(44):14507-14.
Seeman NC, Rosenberg JM, Rich A. Sequence-specific recognition of double helical nucleic acids by proteins. Proc Natl Acad Sci U S A. Mar. 1976;73(3):804-8.
Shaw RW, Clark SD, Hilliard NP, Harman JG. Hyperexpression in *Escherichia coli*, purification, and characterization of the metallo-beta-lactamase of *Bacillus cereus* 5/B/6. Protein Expr Purif. Apr.-Jun. 1991;2(2-3):151-7. (Abstract Only).
Suskovic B, Vajtner Z, Naumski R. Synthesis and Biological Activities of Some Peptidoglycan Monomer Derivatives. Tetrahedron. 1991;47(39):8407-8416.
Sutton BJ, Artymiuk PJ, Cordero-Borboa AE, Little C, Phillips DC, Waley SG. An X-ray-crystallographic study of beta-lactamase II from *Bacillus cereus* at 0.35 nm resolution. Biochem J. Nov. 15, 1987;248(1):181-8.
Thatcher DR. The partial amino acid sequence of the extracellular beta-lactamase I of *Bacillus cereus* 569/H. Biochem J. May 1975;147(2):313-26.
Toney JH, Hammond GG, Fitzgerald PM, Sharma N, Balkovec JM, Rouen GP, Olson SH, Hammond ML, Greenlee ML, Gao YD. Succinic acids as potent inhibitors of plasmid-borne IMP-1 metallo-beta-lactamase. J Biol Chem. Aug. 24, 2001;276(34):31913-8. Epub Jun. 4, 2001.
Tuerk C, Gold L. Systematic evolution of ligands by exponential enrichment: RNA ligands to bacteriophage T4 DNA polymerase. Science. Aug. 3, 1990;249(4968):505-10.
Turner DH, Sugimoto N. RNA structure prediction. Annu Rev Biophys Biophys Chem. 1988;17:167-92.
Yang KW, Crowder MW. Inhibition studies on the metallo-beta-lactamase L1 from Stenotrophomonas maltophilia. Arch Biochem Biophys. Aug. 1, 1999;368(1):1-6.
Zuker M. On finding all suboptimal foldings of an RNA molecule. Science. Apr. 7, 1989;244(4900):48-52.
Ambler RP, Coulson AF, Frere JM, Ghuysen JM, Joris B, Forsman M, Levesque RC, Tiraby G, Waley SG. A standard numbering scheme for the class A beta-lactamases. Biochem J. May 15, 1991;276 ( Pt 1):269-70.
Brown TA. DNA Polymerase I, Klenow Fragment. Molecular Biology Labfax, 2nd ed. 1998;1:147-148.
Ghuysen JM. Evolution of DD-Peptidases and Beta-Lactamases. American Society for Microbiology. 1988:268-284.
Kim SK. Inhibition of Metallo-R-Lactamase by Rational and Combinational Approches. Ph.D. Thesis, Texas Tech University. 2002.

* cited by examiner

Penicillins

Cephalosporins

Penicillins

D-alanyl-D-alanine-peptidoglycan

Transcripts of double-stranded oligomers in a 12% polyacrylamide/7M urea gel.

A complex of the *B. cereus* 5/B/6 metallo-β-lactamase and RNA shown in a 6% polyacrylamide gel.

RT-PCR products on a 6% polyacrylamide gel with a standard base-pair ladder

Determination of $IC_{50}$ for *B. cereus* 5/B/6 metallo-β-lactamase by the 30-mer RNA.

Lineweaver-Burk plot of inhibition of *B. cereus* 5/B/6 metallo-β-lactamase by EDTA.

Lineweaver-Burk plot of inhibition of *B. cereus* 5/B/6 metallo-β-lactamase by the 30-mer RNA.

Inhibition of *B. cereus* 569/H/9 β-lactamase I by various concentrations of the 30-mer RNA.

Inhibition of bovine carboxypeptidase A by various concentrations of the 30-mer RNA.

Determination of $IC_{50}$ for *B. cereus* 5/B/6 metallo-β-lactamase in the presence of $Zn^{2+}$ ions by the 30-mer RNA.

Predicted structures of the 30-mer RNA calculated by MFold program

Secondary structure of 11-mer RNA (a), and secondary structure of 10-mer ssDNA (b).

Determination of $IC_{50}$ for *B. cereus* 5/B/6 metallo-β-lactamase by the 11-mer RNA.

Inhibition of metallo-β-lactamase by 30-mer RNA and 10-mer ssDNA.

| | $IC_{50}$ | $K_i$ | $K_i$' |
|---|---|---|---|
| 30-mer RNA | 11 nM | 2 nM | 15 nM |
| 10-mer ssDNA | 1 nM | 0.31 nM | 1.5 nM |

Figure 18

Reversible inhibition by 30-mer RNA and 10-mer ssDNA.

| | Type of inhibition | $\beta$-lactamase I | carboxypeptidase A |
|---|---|---|---|
| 30-mer RNA | Non-competitive | No inhibition | No inhibition |
| 10-mer ssDNA | Non-competitive | No inhibition | No inhibition |

Figure 19

SEQUENCE LISTING

```
<160> NUMBER OF SEQ ID NOS: 8

<210> SEQ ID NO 1
<211> LENGTH: 88
<212> TYPE: DNA
<213> ORGANISM: Artificial Sequence
<220> FEATURE:
<223> OTHER INFORMATION: 88 mer contain 30 base of randomized sequences
<220> FEATURE:
<221> NAME/KEY: Random
<222> LOCATION: (44)..(73)
<223> OTHER INFORMATION: 88-mer containing 30 bases of randomized
      sequences between two primer regions.
```

<220> FEATURE:
<221> NAME/KEY: misc_feature
<222> LOCATION: (44)..(73)
<223> OTHER INFORMATION: n is a, c, g, or t

<400> SEQUENCE: 1
gcgcatatgc taatacgact cactataggg aacagtccga gccnnnnnnn nnnnnnnnnn 60
nnnnnnnnnn nnncgcgcgg agctcgcg 88

<210> SEQ ID NO 2
<211> LENGTH: 43
<212> TYPE: DNA
<213> ORGANISM: artificial sequence
<220> FEATURE:
<223> OTHER INFORMATION: A 43 mer with a Nde I restriction site for SELEX.

<400> SEQUENCE: 2
gcgcatatgc taatacgact cactataggg aacagtcgca gcc 43

<210> SEQ ID NO 3
<211> LENGTH: 15
<212> TYPE: DNA
<213> ORGANISM: artificial sequence
<220> FEATURE:
<223> OTHER INFORMATION: A 15 mer with a Sac I restriction site for SELEX.

<400> SEQUENCE: 3
cgcgagctcc gcgcg 15

<210> SEQ ID NO 4
<211> LENGTH: 11
<212> TYPE: RNA
<213> ORGANISM: artificial sequence
<220> FEATURE:
<223> OTHER INFORMATION: 11 mer stem loop region

<400> SEQUENCE: 4
gggucuggcc c 11

<210> SEQ ID NO 5
<211> LENGTH: 30
<212> TYPE: RNA
<213> ORGANISM: artificial sequence
<220> FEATURE:
<223> OTHER INFORMATION: This is the 30 mer RNA inhibitor.

<400> SEQUENCE: 5
uggcugcagg gucuggcccc ccguuuggug 30

<210> SEQ ID NO 6
<211> LENGTH: 10
<212> TYPE: DNA
<213> ORGANISM: artificial sequence
<220> FEATURE:
<223> OTHER INFORMATION: 10 mer stem loop DNA

<400> SEQUENCE: 6
ccaaacttgg 10

<210> SEQ ID NO 7
<211> LENGTH: 228
<212> TYPE: PRT
<213> ORGANISM: artificial sequence
<220> FEATURE:
<223> OTHER INFORMATION: This is the amino acid sequence of metallo-b- lactamase

<400> SEQUENCE: 7

```
Met Glu Arg Thr Val Glu His Lys Val Ile Lys Asn Glu Thr Gly Thr
1               5                   10                  15

Ile Ser Ile Ser Gln Leu Asn Lys Asn Val Trp Val His Thr Glu Leu
            20                  25                  30

Gly Tyr Phe Ser Gly Glu Ala Val Pro Ser Asn Gly Leu Val Leu Asn
        35                  40                  45

Thr Ser Lys Gly Leu Val Leu Val Asp Ser Ser Trp Asp Asp Lys Leu
    50                  55                  60

Thr Lys Glu Leu Ile Glu Met Val Glu Lys Lys Phe Lys Lys Arg Val
65                  70                  75                  80

Thr Asp Val Ile Ile Thr His Ala His Ala Asp Arg Ile Gly Gly Met
                85                  90                  95

Lys Thr Leu Lys Glu Arg Gly Ile Lys Ala His Ser Thr Ala Leu Thr
            100                 105                 110

Ala Glu Leu Ala Lys Lys Asn Gly Tyr Glu Glu Pro Leu Gly Asp Leu
        115                 120                 125

Gln Ser Val Thr Asn Leu Lys Phe Gly Asn Met Lys Val Glu Thr Phe
    130                 135                 140

Tyr Pro Gly Lys Gly His Thr Glu Asp Asn Ile Val Val Trp Leu Pro
145                 150                 155                 160

Gln Tyr Gln Ile Leu Ala Gly Gly Cys Leu Val Lys Ser Ala Ser Ser
                165                 170                 175

Lys Asp Leu Gly Asn Val Ala Asp Ala Tyr Val Asn Glu Trp Ser Thr
            180                 185                 190

Ser Ile Glu Asn Val Leu Lys Arg Tyr Gly Asn Ile Asn Leu Val Val
        195                 200                 205

Pro Gly His Gly Glu Val Gly Asp Arg Gly Leu Leu Leu His Thr Leu
    210                 215                 220

Asp Leu Leu Lys
225
```

<210> SEQ ID NO 8
<211> LENGTH: 215
<212> TYPE: PRT
<213> ORGANISM: Artificial Sequence
<220> FEATURE:
<223> OTHER INFORMATION: Consensus sequence of b-lactamase at the 50% level.
<220> FEATURE:
<221> NAME/KEY: misc_feature
<222> LOCATION: (26)..(26)
<223> OTHER INFORMATION: Xaa can be any amino acid.
<220> FEATURE:
<221> NAME/KEY: misc_feature
<222> LOCATION: (172)..(172)
<223> OTHER INFORMATION: Xaa can be any amino acid.

<400> SEQUENCE: 8

```
Val Ile Lys Asn Glu Thr Gly Thr Ile Ser Ile Ser Gln Leu Asn Lys
1               5                   10                  15

Asn Val Trp Val His Thr Glu Leu Gly Xaa Phe Asn Gly Glu Ala Val
            20                  25                  30

Pro Ser Asn Gly Leu Leu Leu Ser Thr Ser Lys Gly Leu Val Leu Val
        35                  40                  45

Asp Ser Ser Trp Asp Lys Leu Thr Lys Glu Leu Ile Glu Met Leu Glu
    50                  55                  60
```

-continued

```
Lys Lys Phe Pro Lys Val Thr Asp Val Ile Ile Thr His Ala His Ala
65                  70                  75                  80

Asp Arg Ile Gly Gly Ile Lys Thr Leu Lys Glu Arg Gly Ile Lys Ala
                85                  90                  95

His Ser Thr Ser Leu Thr Ala Glu Leu Ala Lys Lys Ser Gly Tyr Glu
            100                 105                 110

Glu Pro Leu Gly Asp Leu Gln Ser Leu Thr Ser Leu Lys Phe Gly Asn
        115                 120                 125

Met Lys Val Glu Thr Phe Tyr Pro Gly Lys Gly His Thr Glu Asp Asn
    130                 135                 140

Ile Val Val Trp Leu Pro Gln Tyr Pro Leu Leu Val Gly Gly Cys Leu
145                 150                 155                 160

Val Lys Ser Ala Ala Lys Asp Leu Gly Asn Leu Xaa Asp Ala Tyr Val
                165                 170                 175

Asn Glu Trp Ser Thr Ser Ile Glu Asn Val Leu Lys Arg Tyr Ser Asn
            180                 185                 190

Ile Asn Ala Val Val Pro Gly His Gly Val Gly Asp Gly Leu Leu Leu
        195                 200                 205

His Thr Leu Asp Leu Leu Lys
    210                 215
```

INHIBITION OF METALLO-β-LACTAMASE BY RNA

BACKGROUND

One aspect of the current invention involves nucleic acid ligands that inhibit an activity of lactamase enzymes, wherein the lactamase is a bacterial Class B, metallo-β-lactamase. In a preferred embodiment, a specific 30 mer nucleic acid ligand is used to inhibit a *B. cereus* 5/B/6 metallo-β-lactamase. Another preferred embodiment includes a specific 11 mer nucleic acid ligand is used to inhibit a *B. cereus* 5/B/6 metallo-β-lactamase.

Since the discovery of penicillin, β-lactam antibiotics are among the most prescribed antibacterial chemotherapeutic agents against the treatment for infectious diseases (Maugh, 1981). β-lactam antibiotics, which also include cephalosporins, monobactams and carbapenems, are analogs of peptidoglycans that are involved in the bacterial cell wall synthesis. β-lactam antibiotics target DD-peptidases (D-analyl-D-alanine carboxypeptidases/transpeptidases) that form the peptide cross-links of the peptidoglycan in the final stages of the bacterial cell wall synthesis; this takes place on the external surface of the cytoplasmic membrane and is easily accessible for the antibacterial agents. The β-lactam antibiotics inhibit DD-peptidases by forming a rather stable covalent acylenzyme complex with the DD-peptidases that has a much longer half-life than that formed with the peptidoglycan, thus disrupting the construction of the bacterial cell walls and leading to death of the bacteria (Kelly et al., 1988; Ghuysen, 1988). Because mammalian cells have a different membrane with no cell wall, β-lactams are highly specific for bacteria and even at high concentrations of β-lactams, mammalian cells are not affected.

β-lactam antibiotics all share the presence of the β-lactam ring, a four-membered ring in which a carbonyl and a nitrogen are joined in an amide linkage. FIG. 1 shows the general structures of two classes of β-lactam antibiotics: penicillin and cephalosporin. β-lactam and the adjacent atoms have similar spatial configuration to that of peptidoglycan compounds. The comparison of the structure of penicillins with the structure of D-alanyl-D-alanine-peptidoglycan are shown in FIG. 2. (Suskovic et al., 1991).

A major mechanism of resistance to β-lactam antibiotics is the production of β-lactamases (β-lactamhydrolyases, EC 3.5.2.6). β-lactamases are highly efficient enzymes that catalyze the hydrolysis of the β-lactam rings, thus rendering the loss of bactericidal activity of β-lactam antibiotics. The catalysis of hydrolysis for a generic β-lactam by a β-lactamase is shown in FIG. 3 (Livermore, 1991).

Genes for the production of β-lactamases are widely distributed among bacteria and an increasing number of pathogenic species are found to have developed multiple-drug resistance. Overcoming β-lactamases are of obvious clinical importance and studies of the mechanisms of β-lactamases are vital in the development in new β-lactam antibiotics and β-lactamase inhibitors. Slight alterations in the structures of existing β-lactam antibiotics have been utilized in response to the spread of bacterial drug-resistance; for example, cephalosporins have passed through four generations (Maugh, 1981; Pitout et al., 1997). The use of β-lactam/β-lactamase inhibitor combinations has also increased. There are limits on the chemical manipulation of the existing groups of antibiotics and it is increasingly important to design new types of antibiotics and mechanism-based β-lactamase inhibitors. Because the rational design of a β-lactam antibiotic or β-lactamase inhibitor requires a detailed understanding of the function of β-lactamases, there is great interest in the study of the mechanisms of β-lactamases.

Classification of β-lactamases. A wide range of bacteria produces β-lactamases; an incomplete list of bacteria that produce β-lactamases include *Bacillus cereus, Bacillus fragilis, Escherichia coli, Aeromonous hydrophilia, Bacteroides, Staphylococcus epidermidis, Streptococcus, Pseudomonas aeruginsa, Providencia, Haemophilus, Xanthomonas maltophilia, Acinetobacter, Citrobacter, Enterobacter* and *Branhamella* (Danziger and Pendland, 1997). There are four classes of β-lactamases: class A, B, C and D (Ambler, 1980; Ambler et al., 1991; Joris et al., 1991; Frere, 1995). Class A, C and D β-lactamases are active-site serine enzymes that resemble serine proteases and form an acyl-enzyme intermediate with an active-site serine during the catalysis of β-lactam antibiotics (Rahil and Pratte, 1991). Class A β-lactamases are soluble enzymes as are class D; however, class C β-lactamases are membrane-bound (Hussain, Pastor and Lampen, 1987). Class D β-lactamases do not exhibit primary sequence similarities to class A and C enzymes (Joris et al., 1991; Ledent et al., 1993). Class B β-lactamases are quite different from the other classes; these are metallo-β-lactamases which require divalent metal ion for enzymatic activity (Ambler, 1980; Abraham and Waley, 1979). Native class B enzymes have been isolated with one or two zinc ion(s) bound to their active sites (Carfi et al., 1995; Concha et al., 1996).

The characteristic feature of the substrate profile of class B β-lactamases is that a wide variety of β-lactam antibiotics are hydrolyzed at comparable rates while the other classes of β-lactamases have narrower substrate spectra (Abraham and Waley, 1979). β-lactam antibiotics that are substrates of class B β-lactamases include penicillin derivatives and cephalosporin derivatives (Felici et al., 1993). β-lactam antibiotics, such as carbapenems, cephamycins and imipenems, which are resistant to the serine β-lactamases are hydrolyzed by the class B β-lactamases (Felici et al., 1993; Rasmussen et al., 1994). The inhibitors for other classes of β-lactamases such as penem, 6-β-iodopenicillanic acid and penicillinic acid sulfone, do not inhibit class B β-lactamases (Felici and Amicosante, 1993). A series of mercaptoacetic acid thiol esters (Payne et al., 1997; Yang and Crowder, 1999) and thiomandelic acid (Mollard et al., 2001) have been identified as metallo-β-lactamase inhibitors and understanding the structure and dynamics of metallo-β-lactamases has been studied (Carfi et al., 1995; Concha et al., 1996; Scrofani et al., 1999). However, there is still a need to develop more effective inhibitors of metallo-β-lactamases as these enzymes have been detected in an increasing number of pathogenic bacteria (Neu, H., 1992; Payne et al., 1997).

Metallo-β-lactamase from *Bacillus cereus* 5/B/6. The metallo-β-lactamase was first identified in *B. cereus* 569. It was shown that a part of the cephalosporinase activity in the crude penicillinase preparation from *B. cereus* 569 required $Zn^{2+}$ for maximum activity. The enzyme has unique thermal stability; heating at 60° C. for 30 min. does not abolish the catalytic activity (Crompton et al., 1962; Davies et al., 1974). The first purified metallo-β-lactamase was obtained in a protein-carbohydrate complex (Kuwabara, Adams and Abraham, 1970) from *B. cereus* 569/H, a spontaneous mutant of strain 569 that produces class B β-lactamase constitutively (Kogut et al., 1956). The protein purification was later modified to separate carbohydrate from the protein by gel filtration chromatography (Kuwabara and Lloyd, 1971).

Another *B. cereus* strain 5/B was found to produce one class A β-lactamase and one metallo-β-lactamase; this metallo-β-lactamase is very similar to the metallo-β-lactamase produced by *B. cereus* 569 and 569/H but with slightly different substrate specificity (Crompton et al., 1962). *B. cereus* 5/B/6, a mutant form of *B. cereus* 5/B, only produces the metallo-β-lactamase due to a mutation in the structural gene required for the synthesis of the class A β-lactamase (Davies et al., 1975; Abraham and Waley, 1979). The metallo-β-lactamase from *B. cereus* 5/B/6 was later purified in a similar manner from *B. cereus* 569/H/9 (Thatcher, 1975).

*B. cereus* 569/H/9 and 5/B/6 constitutively produce and secrete large amounts of metallo-β-lactamases and these enzymes, which are isolated with $Zn^{2+}$ at the active site, are among the best-studied class B enzymes (Ambler, 1986; Bicknell et al., 1986; Sutton et al., 1987; Meyers and Shaw, 1989). The metallo-β-lactamases from these two strains are very similar; they both consist of 227 amino acid residues, among which 209 residues are identical (Lim, Pene and Shaw, 1988). Although these β-lactamases are isolated with $Zn^{2+}$ bound at the active site, some other metal ions including $Co^{2+}$, $Cd^{2+}$, $Mn^{2+}$, $Hg^{2+}$ and $Cu^{2+}$ support some catalytic activity of the enzyme (Davies and Abraham, 1974; Hilliard and Shaw, 1992; Hilliard, 1995).

The metallo-β-lactamase from *B. cereus* 5/B/6 has a 29 amino acid leader sequence before it is secreted from the cell. The gene for this enzyme has been cloned, sequenced, and characterized in great detail in *E. coli*. It has also been expressed as an intracellular enzyme with the signal sequence at relatively low levels in *E. coli*; it was also revealed that the metallo-β-lactamases from *B. cereus* strains 5/B/6 and 569/H/9 differ by 18 amino acid residues (Lim, Pene and Shaw, 1988). Even though the procedure for production and purification of metallo-β-lactamase from *B. cereus* 5/B/6 was greatly improved (Meyers and Shaw, 1989), hyperexpression in *E. coli* was still desirable. The cause of the low levels of expression was postulated to be the presence of the 29 amino acid leader peptide at the 5'-end which signals the secretion of the enzyme from *B. cereus* cell (Shaw et al. 1991).

Site-directed mutagenesis was performed to remove the leader sequence and to introduce a NdeI restriction endonuclease site at the initiator codon of the *B. cereus* 5/B/6 β-lactamase structural gene (Shaw et al., 1991); this resulted in the *B. cereus* 5/B/6 β-lactamase structural gene to be in a fragment between a NdeI and a SacI site. This construct allowed the cloning of the *B. cereus* 5/B/6 β-lactamase structural gene into the *E. coli* expression vector pRE2 (Reddy, Peterkofsky and McKenney 1989); this plasmid is denoted at pRE2/b1a. The recombinant plasmid pRE2 was chosen because a gene cloned into its unique NdeI and SacI restriction endonuclease sites within its polylinker region is under the control of its strong λ $P_L$ promoter. In the *E. coli* MZ-1, the temperature sensitive cI repressor binds to the $P_L$ promoter and prevents the expression of the *B. cereus* 5/B/6 β-lactamase gene on plasmid pRE2/bla at low temperatures. At higher temperatures, the cI protein is denatured, thus, allowing the expression of *B. cereus* 5/B/6 β-lactamase at high levels. Subsequent purifications of wild type and mutant *B. cereus* 5/B/6 β-lactamases resulted in a high yield of the metallo-β-lactamases which were identical (Meyers and Shaw 1989; Shaw et al., 1991).

SELEX and enzyme inhibition. In vitro selection, in vitro evolution, and Systematic Evolution of Ligands by Exponential Enrichment ("SELEX") are common names for a technique which allows the simultaneous screening of a large number of nucleic acid molecules for different functionalities. In SELEX, large random pools of nucleic acids can be screened for a particular functionality, such as the binding to small organic molecules (Klug and Famulok, 1994), large proteins (Tuerk and Gold, 1990) or the alteration or de novo generation of ribozyme catalysis (Robertson and Joyce, 1990; Bartel and Szonstale, 1993). Functional molecules are selected from a mainly non-functional pool of RNA or DNA by column chromatography or other selection techniques that are suitable for the enrichment of any desired property.

U.S. Pat. No. 5,637,459 entitled "Systematic Evolution of Ligands by Exponential Enrichment: Chimeric Selex" issued on Jun. 30, 1998 with Burke et al., listed as inventors, and U.S. Pat. No. 5,773,598 entitled "Systematic Evolution of Ligands by Exponential Enrichment: Chimeric Selex" issued on Jun. 30, 1998 with Burke et al., listed as inventors, both of these patents describe and elaborate on the SELEX process in great detail. Both cited patents are herein incorporated by reference. Included are targets that can be used in the process; methods for partitioning nucleic acids within a candidate mixture; and methods for amplifying partitioned nucleic acids to generate enriched candidate mixture. The SELEX Patents also describe ligands obtained to a number of target species, including both protein targets where the protein is and is not a nucleic acid binding protein.

SELEX method is conceptually straightforward. A starting, degenerate oligonucleotide pool is generated using a standard DNA-oligonucleotide synthesizer; the instrument synthesizes an oligonucleotide with a completely random base-sequence, which is flanked by defined primer binding sites. The immense complexity of the generated pool justifies the assumption that it may contain a few molecules with the correct secondary and/or tertiary structures that bind tightly and specifically to a target enzyme and inhibit the enzymatic activity. These molecules are selected, for example, by affinity chromatography or filter binding. Because a large, random pool can be expected to contain only a very small number of functional molecules, several purification steps are required. Only "active" molecules are amplified by polymerase chain reaction (PCR). Iterative cycles of selection are carried out for successive selection and amplification cycles in the exponential increase in the abundance of functional sequences, until they dominate the population.

A pool of 88-mer oligonucleotides containing an internal 30-nucleotide random sequence were synthesized; this would give a possibility of $4^{30}$ ($1.2\times10^{18}$) different sequences projected from the possibility of any four nucleotides in 30 positions. The internal 30-nucleotide region is flanked by defined primer sites which are 43 and 15 nucleotides at their 5' and 3' termini, respectively. These were later transcribed and the single-stranded RNA has been selected that not only binds tightly and specifically to the *B. cereus* 5/B/6 metallo-β-lactamase but also inhibits this enzyme.

Prediction of secondary structure of aptamers. MFold program is an adaptation of the MFold package (version 2.3) by Zuker (1989) and Jaeger et al. (1989, 1990) that has been modified to work with the Wisconsin Package™. Their method uses the energy rules developed by Freier et al. (1986) to predict optimal secondary structures for an RNA molecule and the energy rules complied and developed by Turner et al. (1988) to predict optimal and sub-optimal secondary structures for a single-stranded RNA molecule. This approach can provide a first-approximation prediction of a nucleic acid secondary structure from a nucleic acid sequence.

The invention described herein has utilized the method of SELEX to develop nucleic acid ligands for a lactamase enzyme. The nucleic acid ligands are utilized as metallo-β-lactamase inhibitors.

SUMMARY

Generally, the current invention comprises high affinity polyribonucleiotides useful for inhibiting the activity of bacterial lactamase enzymes. More specifically, the current invention involves relatively short high affinity polyribonucleiotides ligands that inhibit an activity of Class B metallo-β-lactamase. In a preferred embodiment, a 30 mer polyribonucleotide selectively binds the Class B lactamase. In another preferred embodiment, an 11 mer polyribonucleotide selectively binds the Class B lactamase. Both the 30-mer and 11 mer polyribonucleotides specifically inhibit *B. cereus* 5/B/6 metallo-β-lactamase.

The method used to generate the high affinity polyribonucleiotides comprises several steps that initially involve preparing a candidate mixture of nucleic acids. The candidate mixture of nucleic acids is then allowed to make contact with the lactamase enzyme under controlled conditions of temperature, ionic strength and pH; the combination forms a candidate-enzyme mixture. Not all candidates bind tightly to the enzyme. The target nucleic acids may be easily partitioned from the remainder of the candidate mixture. Partitioning the target-nucleic acids from the remainder of the candidate mixture can be performed by many methods known to one skilled in the art. Once the target nucleic acids have been partitioned, they can be amplified to yield a pool of nucleic acids enriched with target nucleic acid sequences. The enriched pool of target nucleic acids have a relatively higher affinity and specificity for binding to the lactamase, whereby nucleic acid ligand of the lactamase may be identified through methods known to one skilled in the art of molecular biology (e.g. DNA and RNA sequencing).

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 18 shows inhibition of metallo-β-lactamase by 30-mer RNA and 10-mer ssDNA;

FIG. 19 shows types of inhibition by 30-mer RNA and 10-mer ssDNA; and

DETAILED DESCRIPTION OF PREFERRED EMBODIMENTS

Terms

Figure 1:
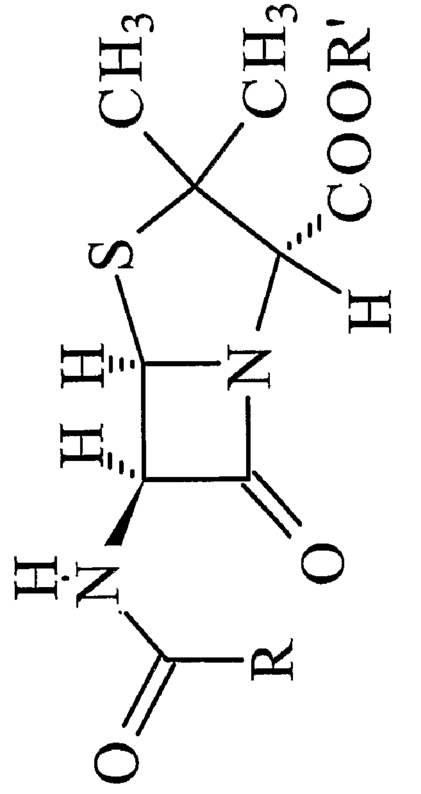
FIG. 1 shows structures of two classes of β-lactam antibiotics: Penicillins and Cephalosporin.
Figure 1:
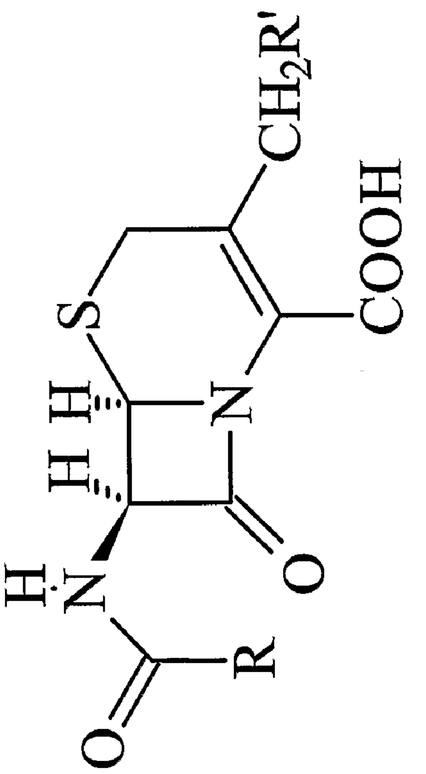
Figure 2:
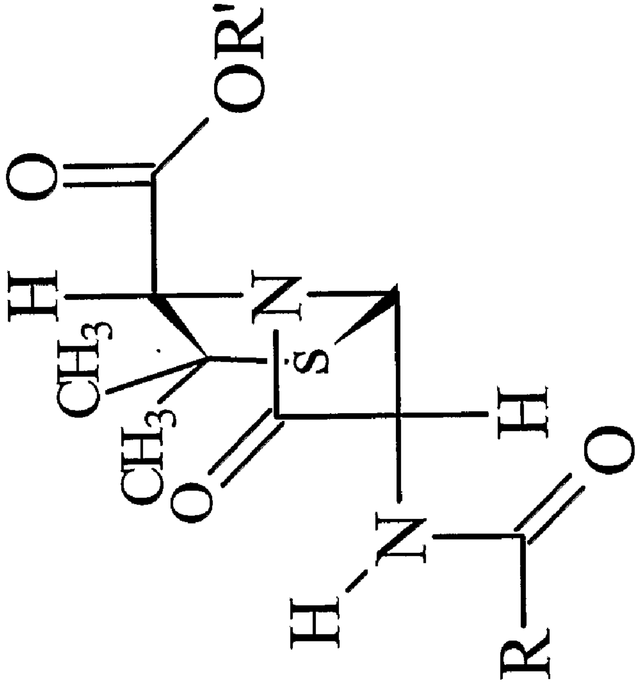
FIG. 2 shows the comparison of the structure of penicillins with the structure of D-alanyl-D-alanine-peptidoglycan.
Figure 2:
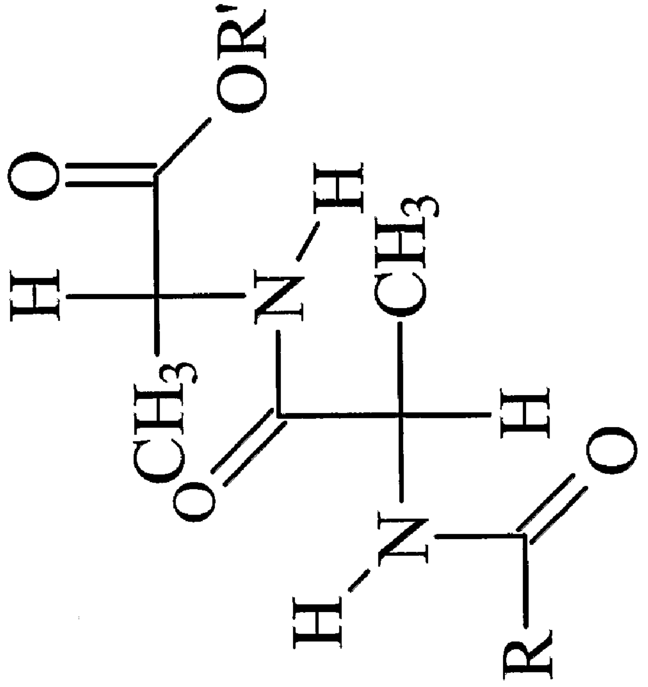
Figure 3:
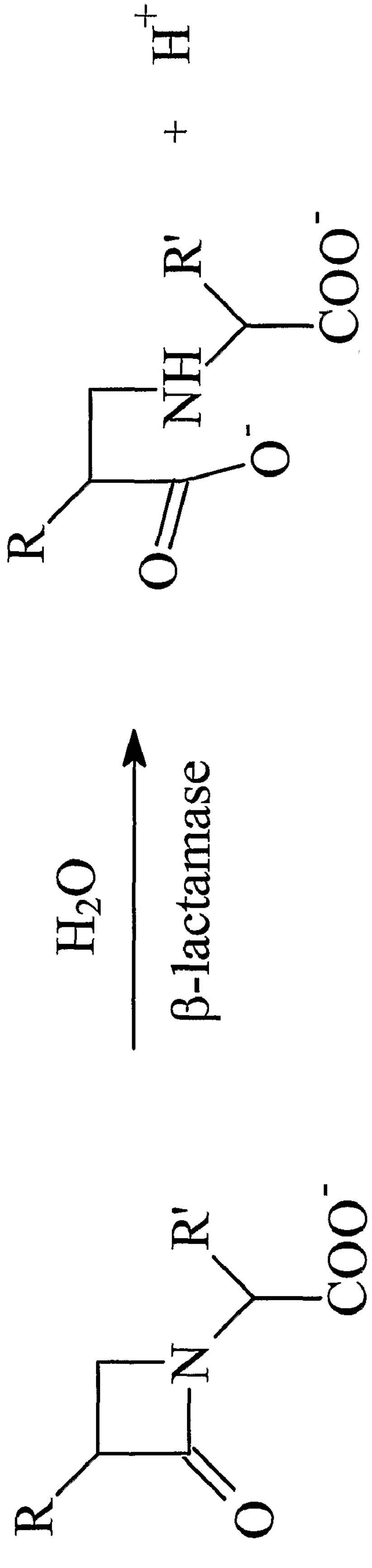
FIG. 3 shows catalysis of hydrolysis of a generic β-lactam by a β-lactamase.

The term "binding" of a polyribonucleotide to a metalloenzyme, typically is performed under moderate to stringent enzyme binding conditions. Stringent conditions include, incubating in NaCl concentrations in the range of 10 to 20 mM. Additional guidance regarding such conditions is readily available in the art, for example, (WO 2004/031142 A2 entitled "Inhibition of Metallo-Beta-Lactamase" published on Apr. 15, 2004 with Shaw et al., listed as inventors.)

The term "candidate mixture" is a mixture of nucleic acids of differing sequence from which to select a desired ligand. The source of a candidate mixture can be from naturally occurring nucleic acids or fragments thereof, chemically synthesized nucleic acids, enzymatically synthesized nucleic acids or nucleic acids made by a combination of the foregoing techniques. In a preferred embodiment, each nucleic acid has fixed sequences surrounding a randomized region to facilitate the amplification process.

The term "complementary" means that one nucleic acid molecule has the sequence of the binding partner of another nucleic acid molecule. Thus, the sequence 5'-ATGC-3' is complementary to the sequence 5'-GCAT-3'.

The term "codon" as used herein refers to any group of three consecutive nucleotide bases in a given messenger RNA molecule, or coding strand of DNA that specifies a particular amino-acid, or a starting or stopping signal for translation. The term codon also refers to base triplets in a DNA strand.

The term "coding region" as used herein refers to any portion of the DNA sequence that is transcribed into messenger RNA (mRNA) and then translated into a sequence of amino acids characteristic of a specific polypeptide.

The term "heterologous nucleic acid sequence" as used herein is defined as a DNA sequence consisting of differing regulatory and expression elements.

The term "hybridization" signifies hybridization under conventional hybridizing conditions, preferably under stringent hybridization conditions, as described for example in Sambrook et al., Molecular Cloning, A Laboratory Manual, 2nd Edition (1989) Cold Spring Harbor Laboratory Press, Cold Spring Harbor, N.Y.).

The term "identical" in the context of two nucleic acid or polypeptide sequences refers to the residues in the two sequences which are the same when aligned for maximum correspondence. When percentage of sequence identity is used in reference to proteins or peptides it is recognized that residue positions which are not identical often differ by conservative amino acid substitutions, where amino acids residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a fill mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to known algorithm. See, e.g., Meyers and Miller, Computer Applic. Biol. Sci., 4:11-17 (1988); Smith and Waterman (1981) Adv. Appl. Math. 2:482; Needleman and Wunsch (1970) J. Mol. Biol. 48:443; Pearson and Lipman (1988) Proc. Natl. Acad. Sci. USA 85:2444; Higgins and Sharp (1988) Gene, 73:237-244 and Higgins and Sharp (1989) CABIOS 5:151-153; Corpet, et al. (1988) Nucleic Acids Research 16, 10881-90; Huang, et al. (1992) Computer Applications in the Biosciences 8, 155-65, and Pearson, et al. (1994) Methods in Molecular Biology 24, 307-31. Alignment is also often performed by inspection and manual alignment.

A "labile ligand" as used herein means a nucleic acid ligand identified by the SELEX process that has a greatly decreased affinity for its target based on an adjustment of an environmental parameter. In the preferred embodiment, the environmental parameter is temperature, and the affinity of a ligand to its target is decreased at elevated temperatures.

"Nucleic Acid" means either DNA, RNA, single-stranded or double-stranded and any chemical modifications thereof. Modifications include, but are not limited to, those that provide other chemical groups that incorporate additional charge, polarizability, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil, backbone modifications, methylations, unusual base-pairing combinations such as the isobases isocytidine and isoguanidine and the like. Modifications can also include 3' and 5' modifications such as capping.

"Nucleic Acid Ligand" as used herein is a non-naturally occurring nucleic acid having a desirable action on a target. A desirable action includes, but is not limited to, binding of the target, catalytically changing the target, reacting with the target in a way which modifies/alters the target or the functional activity of the target, covalently attaching to the target as in a suicide inhibitor, facilitating the reaction between the target and another molecule. In the preferred embodiment, the action has specific binding affinity for a target molecule, such target molecule being a three dimensional chemical structure other than a polynucleotide that binds to the nucleic acid ligand, wherein the nucleic acid ligand is not a nucleic acid having the known physiological function of being bound by the target molecule. The target molecule in a preferred embodiment of this invention is a lactamase. Nucleic acid ligands include nucleic acids that are identified from a candidate mixture of nucleic acids, said nucleic acid ligand being a ligand of a given target by the method comprising: a) contacting the candidate mixture with the target, wherein nucleic acids having an increased affinity to the target relative to the candidate mixture may be partitioned from the remainder of the candidate mixture; b) partitioning the increased affinity nucleic acids from the remainder of the candidate mixture; and c) amplifying the increased affinity nucleic acids to yield a ligand-enriched mixture of nucleic acids.

"SELEX" methodology involves the combination of selection of nucleic acid ligands that interact with a target in a desirable manner, for example binding to a protein, with amplification of those selected nucleic acids. Iterative cycling of the selection/amplification steps allows selection of one or a small number of nucleic acids that interact most strongly with the target from a pool that contains a very large number of nucleic acids. Cycling of the selection/amplification procedure is continued until a selected goal is achieved. In the present invention, the SELEX methodology is employed to obtain nucleic acid ligands to a lactamase enzyme.

The term "Target" means any compound or molecule of interest for which a ligand is desired. A target can be a protein, peptide, carbohydrate, polysaccharide, glycoprotein, hormone, receptor, antigen, antibody, virus, substrate, metabolite, transition state analog, cofactor, inhibitor, drug, dye, nutrient, growth factor, etc. without limitation. In this application, the target is a lactamase. In a preferred embodiment the lactamase is a class B metallo-lactamase.

Example 1

The invention comprises general and specific methods and compositions for producing inhibitors for Metallo-β-lactamase, including SELEX technology. Although specific materials and methods have been used as illustrative examples, other similar types of materials and methods that inhibit Metallo-β-lactamase using nucleic acids are not considered to deviate from the spirit and scope of the claimed invention.

Metallo-β-lactamase. Metallo-β-lactamase from *B. cereus* 5/B/6 was produced from *E. coli* TAP56 carrying the pRE2/b1a plasmid and purified according to procedures described previously (Shaw et al., 1991). The purity of the enzyme was ascertained by specific activity, native and SDS-PAGE, and DE-MALDI-TOF. T4 DNA ligase was purchased from Promega. Restriction endonucleases NdeI and SacI were purchased from New England Biolabs, Inc. and were used according to manufacturer's recommendations. DNA molecular weight markers, BstNI digested pBR322 and BstEII digested λ DNA, were purchased from New England Biolabs, Inc. DEAE-Sephacel, Sephadex G-25 (superfine) and CM-Sepharose CL 6B and various columns were purchased from Pharmacia or Bio-Rad Laboratories. The Gene Clean II Kit was purchased from BIO101. The 88-mer was purchased from Midland Certified Reagent Company. PCR reactions were carried out using a Perkin Elmer Certus Thermal Cycler. Pfu polymerase was purchased from Stratagene. The cell suspensions were sonicated using a Heat System Ultrasonics, Inc. model W-375 sonicator. PCI (phenol: chloroform: isoamyl alcohol (25:24:1)) and electrophoresis grade agarose were obtained from Amresco. Bovine carboxypeptidase A and hippuryl-L-phenylalanine were purchased from Sigma. PCR 20 bp low ladder, ethidium bromide, dimethylsulfoxide (DMSO), acrylamide, bisacrylamide, benzylpenicillin, cephalosporin C (potassium salt), ampicillin, ethylendiaminetetraacetic acid (EDTA), ethanol, glucose, sodium hydroxide (NaOH), potassium hydroxide (KOH), N-2-hydroxyethylpiperazine-N'-2-ethanesulfonic acid (HEPES), rubidium chloride, urea, 3-[N-morpholino]propanesulfonic acid (MOPS), Tris, $ZnSO_4$, deoxyribonucleoside triphosphates (dNTPs), ribonucleoside triphosphates (NTPs), dithiothreitol (DTT) and various other inorganic salts and organic solvents of reagent grade or better were obtained form Sigma Chemical Co. Difco brand bacto-agar, casamino acids and yeast extract used to make all media and plates were obtained through Fisher Scientific.

Assay of the purified *B. cereus* 5/B/6 metallo-β-lactamase and *B. cereus* 569/H/9 β-lactamase I. Metallo-β-lactamase activity assays using cephalosporin C as substrate were determined as previously reported (Myers and Shaw, 1989). The cephalosporin C absorbance maximum at 260 nm was monitored as a function of time (Davies et al., 1974). One unit of activity is generally defined as the amount of enzyme required to catalyze the hydrolysis of about 1 μmol of β-lactam substrate (cephalosporin C) per minute at 30° C. at pH 7.0. All activity assays were carried out near $V_{max}$ using 4.3 mM cephalosporin C dissolved in 50 mM MOPS/1 mM ZnSO4, pH 7.0 buffer. The assays were carried out at 30° C. in a 0.1 cm path length quartz cell and the total assay volume was 250 µL.

The β-lactamase I activity assays used was modified from Davies et al. (1974), which described a general method of β-lactamase I activity assays. Briefly, the enzyme was incubated with 20 mM EDTA (pH 7.0) for 15 min. at room temperature prior to the assay. The enzymatic hydrolysis of 1.1 mM benzylpenicillin in 10 mM MOPS (pH 7.0) and 1 mM EDTA was continuously monitored at 231 nm at 30° C. in a 1-cm pathlength quartz cell in a total volume of 1 mL. One unit of β-lactamase activity was generally defined as the amount of enzyme required to hydrolyze about one µmole of substrate/min. at 30° C. at pH 7.0.

The protein concentrations were determined by the method of Lowry (Lowry et al., 1951) using bovine serum albumin as a standard. This method was used throughout for all protein determinations.

Assay of bovine carboxypeptidase A. The assay of bovine carboxypeptidase A is based on the method of Folk and Schirmer (1963). The rate of hydrolysis of hippuryl-L-phenylalanine is determined by monitoring the increase in absorbance at 254 nm (25° C., pH 7.5). The enzyme was dissolved in 10% lithium chloride to a concentration of 1-3 units per mL. Hippuryl-L-phenylalanine (0.001 M) was dissolved in 0.05 M Tris-HCl, pH 7.5, with 0.5 M sodium chloride. In a 1-cm pathlength cuvette, 1.0 mL of substrate was added and incubated in the spectrophotometer at 25° C. for 3-4 minutes to reach temperature equilibration and to establish blank rate. 50 µL of diluted enzyme was added to record the increase in $AbS_{254}$.

Reversible inhibition studies for metallo-β-lactamase. To test for reversible inhibition, metallo-β-lactamase was incubated with various concentrations of the possible inhibitors in 50 mM MOPS buffer, pH 7.0. The enzyme activity remaining was determined (Myers and Shaw, 1989).

SELEX. An 88-mer oligonucleotide was synthesized by The Midland Certified Reagent Company. This 88-mer contained 30 bases of randomized sequence between two primer regions encompassing SacI and NdeI recognition sites Seq ID No.: 1:

```
5'-GCGCATATGCTAATACGACTCACTATAGGGAAGAGTCCGAGCC-
NdeI

(N)30-CGCGCGGAGCTCGCG-3'
      SacI
```

The 5'-end and 3'-end primers were synthesized using a Beckman Instruments, Inc. OLIGO 1000 M DNA synthesizer:

5'-end primer: (43-mer) possessing NdeI site (Seq ID No. 2):

```
5'-GCGCATATGCTAATACGACTCACTATAGGGAACAGTCGCAGCC-3'
NdeI
```

3'-end primer: (15-mer) possessing SacI site (Seq ID No. 3):

```
5'-CGCGAGCTCCGCGCG-3'
```

SacI

Double-stranded 88-mer. To anneal the 3'-end primer to the 88-mer, the following steps were performed. 75 pmol of 88-mer, 150 pmol of 3'-end primer and 500 mM NaCl in a total reaction volume of 100 µL were incubated at 92° C. for one minute. The reaction was cooled to room temperature and the oligonucleotides were precipitated by adding 2.5 volumes of cold ethanol. This was placed in −4° C. for one hour. The primer was extended to synthesize the second strand by the following: 0.5 mM dNTPs, 100 mM HEPES/NaOH, pH 6.9, 70 mM KCl, 10 mM $MgCl_2$, 2.5 mM DTT were added to the primed 88-mer in a total reaction of 10 µL. One hundred units of Klenow enzyme were added to the reaction and the mixture was incubated at room temperature for one hour. Another 100 units of Klenow enzyme were added and the mixture was incubated for another hour at room temperature. The enzyme was extracted by adding an equal volume of phenol:chloroform:isoamyl alcohol (PCI) and vortexed for one minute; the mixture was centrifuged for one minute to separate the aqueous layer and the top layer was saved. An equal volume of chloroform:isoamyl alcohol (CI) was added and the mixture was vortexed and centrifuged for one minute each. The top layer was saved for ethanol precipitation.

Transcription. For production of ssRNAs, 3 mM ribonucleoside triphosphates (NTPs), 1 mM $MgCl_2$, 200 mM HEPES-KOH, pH 8.0, 40 mM dithiothreitol (DTT) and 2 mM spermidene were added to the dsDNA mixture to a total volume of 20 µL. This was incubated at 37° C. for one hour with 20 units of T7 RNA polymerase. 2 units of DNase were added and the reaction was incubated at 37° C. for 15 minutes to denature the DNA. This was followed by PCI/CI extraction to extract the enzymes. One-tenth volume of 5 M ammonium acetate was added with ethanol for ethanol precipitation. The RNA products were separated on a 12% (w/v) polyacrylamide/7M urea gel as previously described in Molecular Cloning: A Laboratory Manual (Sambrook, Fritsch, and Maniatis, 1989). The resulting gel was soaked in incubation buffer with ethidium bromide for 10 minutes and destained in $d_2H_20$ for ten minutes. The RNA products were visualized by UV illumination using TM-36 Chromato-UVE transilluminator from UVP Inc. and were excised. The RNA bands were extracted by a modified crush and soak method (Maxam and Gilbert, 1977) with the following modifications: the bands were crushed in a microcentrifuge tube using a disposable pipette tip. The bands were weighed to determine their total weight and 0.1 mL of elution buffer (0.5 M ammonium acetate, 1 mM EDTA, pH 8.0, and 0.1% (w/v) SDS) was added for every gram of gel bands. The tubes were incubated at 45° C. on a rotary platform for 2.5-3.0 hours. The tubes were then centrifuged at 12,000 g for 1 minute and the supernatant was transferred to a new microcentrifuge tube containing a plastic column packed with glass wool. A one-half volume of elution buffer was added to the remaining gel pieces to be vortexed and centrifuged. The additional supernatant was added to the column/tube and the column/tube was centrifuged for 15 seconds to separate the gel pieces from the supernatant and to collect the supernatant in the microcentrifuge tube. 2.5 volumes of ethanol and $1/10^{th}$ volume of 5 M ammonium acetate were added for ethanol precipitation of the recovered RNA products.

Gel shift assay. The electrophoretic mobility shift assay used 6% (w/v) polyacrylamide gels (29:1 mono:bis) in 20 mM Tris-acetate (TA) buffer, pH 7.0, polymerized with 0.07% (w/v) ammonium persulfate and 0.028% (v/v) TEMED. The stock enzyme in 150 mM ammonium sulfate, 10 mM sodium citrate, pH 7.0, 1 mM ZnSO4, and 30% (v/v) glycerol, was heated for 30 minutes at 60° C. to denature any possible other proteins. The enzyme was centrifuged for one minute and the supernatant was collected. The enzyme was diluted with dilution buffer (20 mM TA and 1 mM ZnSO4, pH 7.0). The purified RNA products were used for SELEX selection. The RNA products were incubated with enzyme at 30° C. for 15 minutes in TA buffer in a total reaction volume of 20 μL. In order to gradually increase the stringency of inhibitor binding, increasing concentrations of NaCl were added to the incubation of the RNA products with the enzyme. In rounds 5-8, the NaCl concentration was 10 mM; in rounds 9-12, the NaCl concentration was 20 mM. After 15 minutes, 5 μL 40% (v/v) glycerol was added to the sample and the 6% (w/v) polyacrylamide gel was run at 200 V for 25-30 minutes. The enzyme:RNA complex band was excised, crushed and soaked and ethanol-precipitated as previously described.

Reverse transcription/PCR. For production of cDNAs, 500 μM deoxynucleotide triphosphates (dNTPs) and 10 ng of 3'-end primer were added to the recovered RNAs to a total reaction volume of 17.0 μL. This was incubated at 85° C. for 10 minutes and placed on ice. Two μL of 10X RT-PCR buffer and 100 units of reverse transcriptase were added; this was incubated at 42° C. for 50 minutes. For amplification of cDNAs, the following steps were taken. Ten μL of 10X Pfu buffer, 0.2 mM dNTPs, 250 ng of 5'-end primer, 250 ng of 3'end primer and 2.5 units of Pfu enzyme were added to 5.0 μL of cDNA solution to a total reaction volume of 100 μL. The reaction was subjected to 30 cycles at 94° C. for 45 sec, 40° C. for 45 sec, and 72° C. for 11 sec. This was followed by 10 minutes at 72° C. to allow all annealed primers to finish extending. The PCR products were purified from 6% (w/v) polyacrylamide gel as described above.

Cloning and sequencing. The plasmid pRE2 was digested with restriction endonucleases NdeI and SacI. The linerarized pRE2 vector was electrophoretically separated on 1.0% (w/v) agarose gel in 0.045 M Tris-borate/0.001 M EDTA (TBE) buffer at 60 V for 3 hours. The linearized pRE2 vector was located by staining the gel in 5 μg/mL ethidium bromide solution and visualized under UV. The bands were excised from gel and were extracted by the Gene Clean Kit (purchased from BIO 101).

The purified PCR products described above were also digested with restriction endonucleases NdeI and SacI and purified on a 6% (w/v) polyacrylamide gel.

Digested PCR products were ligated into linear pRE2 vector with T4 DNA ligase (purchased from Promega Co.) at 4° C. overnight. For each ligation, 300 ng of linearized pRE2 vector, 10 ng of PCR products and 3 units of T4 DNA ligase were mixed together in ligation buffer in a total reaction volume of 10 μL. After incubation, the mixture was used to transform *E. coli* strain TAP 56 competent cells prepared by the Hanahan method (Hanahan, 1983). The resultant colonies were grown in an LB medium, pH 7.0, of 1.0% (w/v) casamino acid, 0.5% (w/v) yeast extract, 0.5% (w/v) sodium chloride and 50 μg/mL ampicillin. The culture was incubated at 30° C. overnight. The subcloned plasmid DNA was purified using QIAprep Spin Miniprep kit (purchased from Qiagen, Inc.). The purified plasmid was sequenced by an ABI PRISMTM 310 Genetic Analyzer. After finding the sequence, the 30-mer insertion was synthesized by Integrated DNA Technologies.

Inhibition assays of 30-mer RNA and random pool RNA. Various assays were conducted with the 30-mer RNA in the presence of metallo-β-lactamase to determine its inhibition values ($IC_{50}$, $K_i$, and $K_i'$). The 30-mer RNA was tested for inhibition of β-lactamase I and bovine carboxypeptidase A. The 30-mer RNA was also tested for inhibition of metallo-β-lactamase in the presence of $Zn^{2+}$.

A pool of degenerate RNA before the first incubation with enzyme was synthesized as described in Methods and tested for inhibition of metallo-β-lactamase.

Prediction of secondary structures of RNA. The secondary structure of the 30-mer RNA was predicted by the MFold program (Zuker, 1989). Three different secondary structures of the 30-mer RNA were predicted; the structure predicted with the lowest energy showed an 11-mer loop region (SEQ ID NO. 4): 5'-GGGUCUGGCCC-3'. This loop shows the closest homology to a previously determined 10-mer ssDNA inhibitor of metallo-β-lactamase (S. K. Kim, 2002) and this result suggests that the loop structure may be important for interaction with metallo-β-lactamase.

To confirm the loop structure of the 11-mer, the secondary structure of the 11-mer was predicted by the MFold program and the 11-mer RNA sequence was synthesized by Integrated DNA Technologies. The 11-mer RNA was tested for inhibition of metallo-β-lactamase.

Example 2

Combinatorial approach to inhibition of metallo-β-lactamase: SELEX. A pool as many as $4^{30}$ ($1.2\times10^{18}$) 88-mer oligonucleotides was synthesized. The complimentary strands of the 88-mer were synthesized and the double-stranded oligomers were amplified by PCR. The PCR products were purified through a native polyacrylamide gel and this was followed by transcription of the double-stranded oligomers and purification of the RNA products from a denaturing gel.

Figure 4:
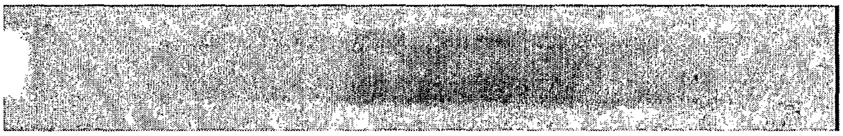
FIG. 4 shows transcripts of double-stranded oligomers in a 12% polyacrylamide/7M urea gel.

FIG. 4 shows the various RNA products that were produced. The transcripts shown in FIG. 4 are double-stranded oligomers in a 12% polyacrylamide/7M urea gel. The figure shows a band of the full-length transcripts followed by various migrations of incomplete transcripts. The transcripts were purified from the denaturing polyacrylamide gel and the pool of RNA was incubated with metallo-β-lactamase to form an enzyme:RNA complex.

Figure 5:
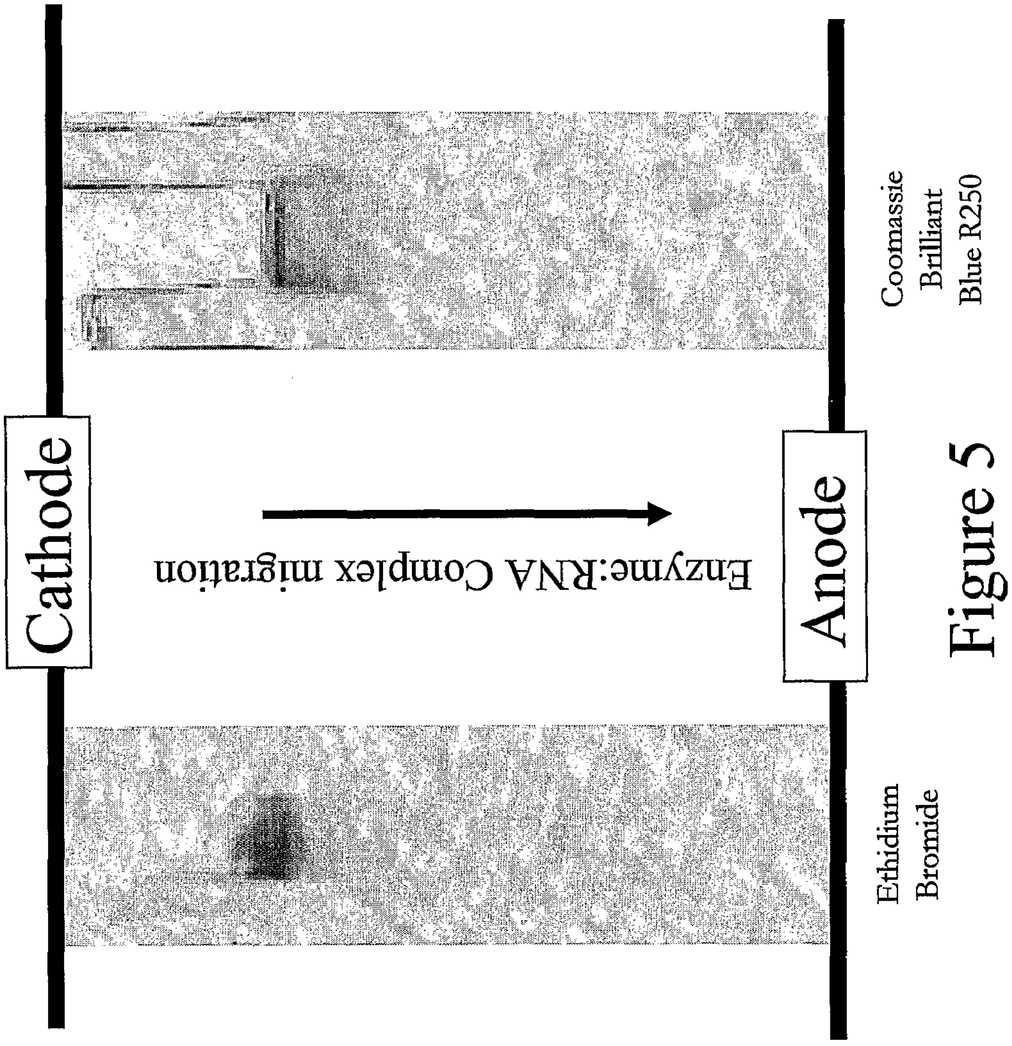
FIG. 5 shows the evidence for a complex of the *B. cereus* 5/B/6 metallo-β-lactamase and the RNA.

The enzyme:RNA complex was then separated from unbound RNA by electrophoresis. As shown in FIG. 5A, the enzyme bound RNAs are visualized using an ethidium bromide staining procedure. The *B. cereus* 5/B/6 metallo-β-lactamase is a cationic enzyme. Although not wanting to be bound by theory, if there were no RNA binding to the enzyme, the enzyme would not migrate into the gel but would rather travel toward the cathode and out of the sample well area. The bound RNA provides negative charges for migration through the gel toward the anode. The bound RNA can be visualized by ethidium bromide fluorescence (FIG. 5A) and the enzyme can be visualized by Coomassie Brilliant Blue R250 staining (FIG. 5B). The complex of the *B. cereus* 5/B/6 metallo-β-lactamase and the RNA shown in FIG. 5 was separated in a 6% polyacrylamide gel.

As noted previously, the concentration of salt added to the incubation of RNA with enzyme was increased with successive rounds, which was used to increase the stringency of selection during the course of the SELEX rounds. The range of salt concentrations used to increase stringent conditions were from about 10 mM to about 20 mM. The electrophoretic separation allows the visualization of each selection round, thus, revealing whether ligand binding has occurred and the making apparent the relative amounts of bound RNA.

Figure 6:
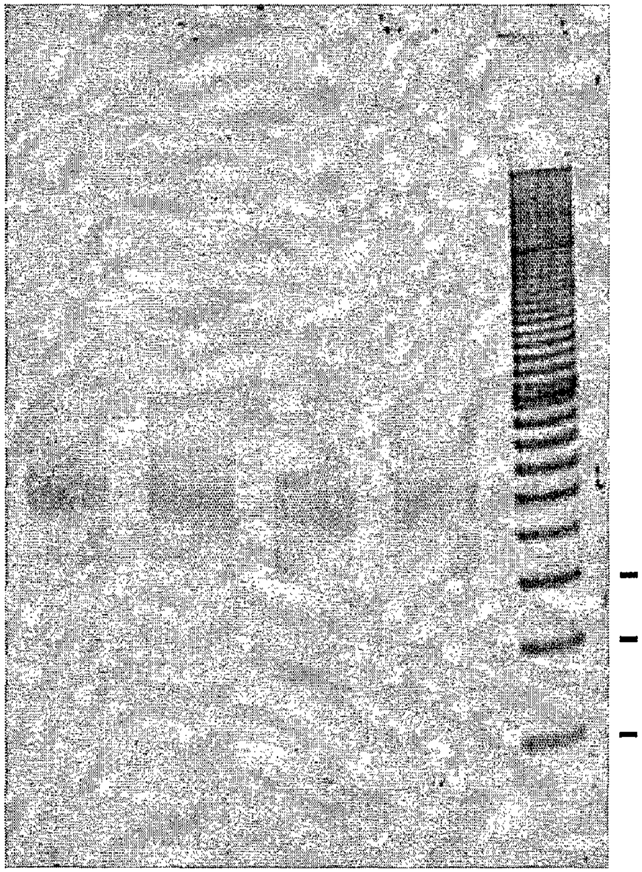
FIG. 6 shows RT-PCR products.

The bound RNA was purified from the gel and the cDNA was synthesized by reverse transcription. This was followed by another round of PCR which amplified the selected RNA products in their dsDNA form. FIG. 6 shows a round of PCR products which run right above the 80 base-pair ladder. This step shows the completion of one cycle of SELEX and that "active" RNA products are purified and amplified through SELEX. The RNA products shown in FIG. 6 were separated using a 6% polyacrylamide gel, wherein Lanes 1-4 shown the RT-PCR products and Lane 5 shows a standard base-pair ladder.

This process was repeated through twelve rounds. After the twelfth round, the PCR products were cloned into the vector pRE2 and the plasmid was sequenced.

The sequence of the 30-mer region (SeqID No.: 5) is shown:

```
5'-UGG CUG CAG GGU CUG GCC CCC CGU UUG GUG-3'
```

The 30-mer RNA was synthesized by MoleculA and Integrated DNA Technologies and was tested for inhibition of metallo-β-lactamase and other enzymes.

Figure 7:
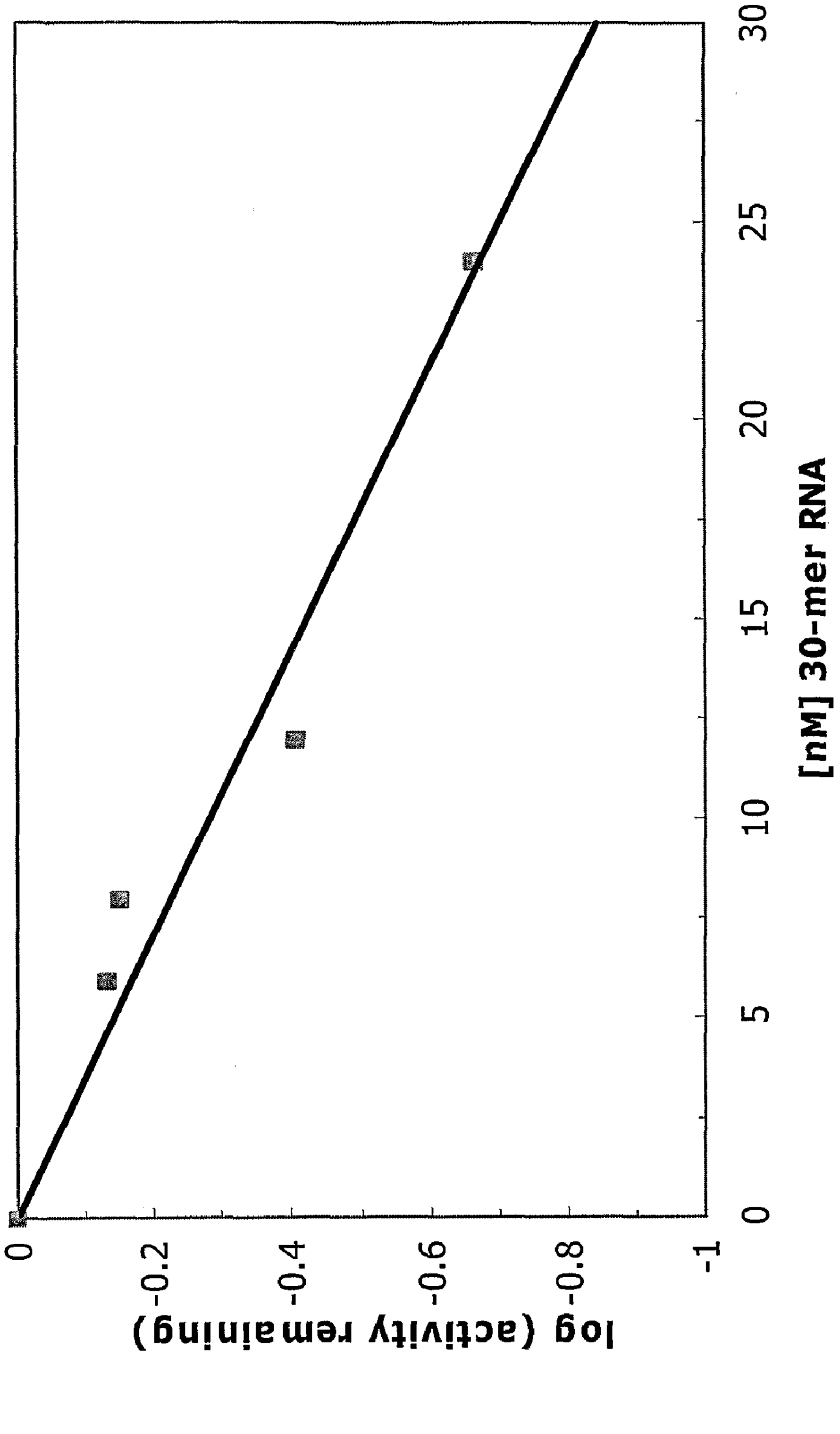
FIG. 7 shows the determination of $IC_{50}$ for *B. cereus* 5/B/6 metallo-β-lactamase by the 30-mer RNA.

30-mer RNA. The $IC_{50}$ value for the 30-mer RNA was determined by measuring the rate of enzymatic hydrolysis of cephalosporin C with different amounts of the 30-mer RNA. The determination of $IC_{50}$ for *B. cereus* 5/B/6 metallo-β-lactamase by the 30-mer RNA was determined and the concentration of the substrate (cephalosporin C) was 4.3 mM in the buffer (50 mM MOPS, pH 7.0). Thus, the $IC_{50}$ of the 30-mer was 11 nM, as shown in FIG. 7.

Figure 9:
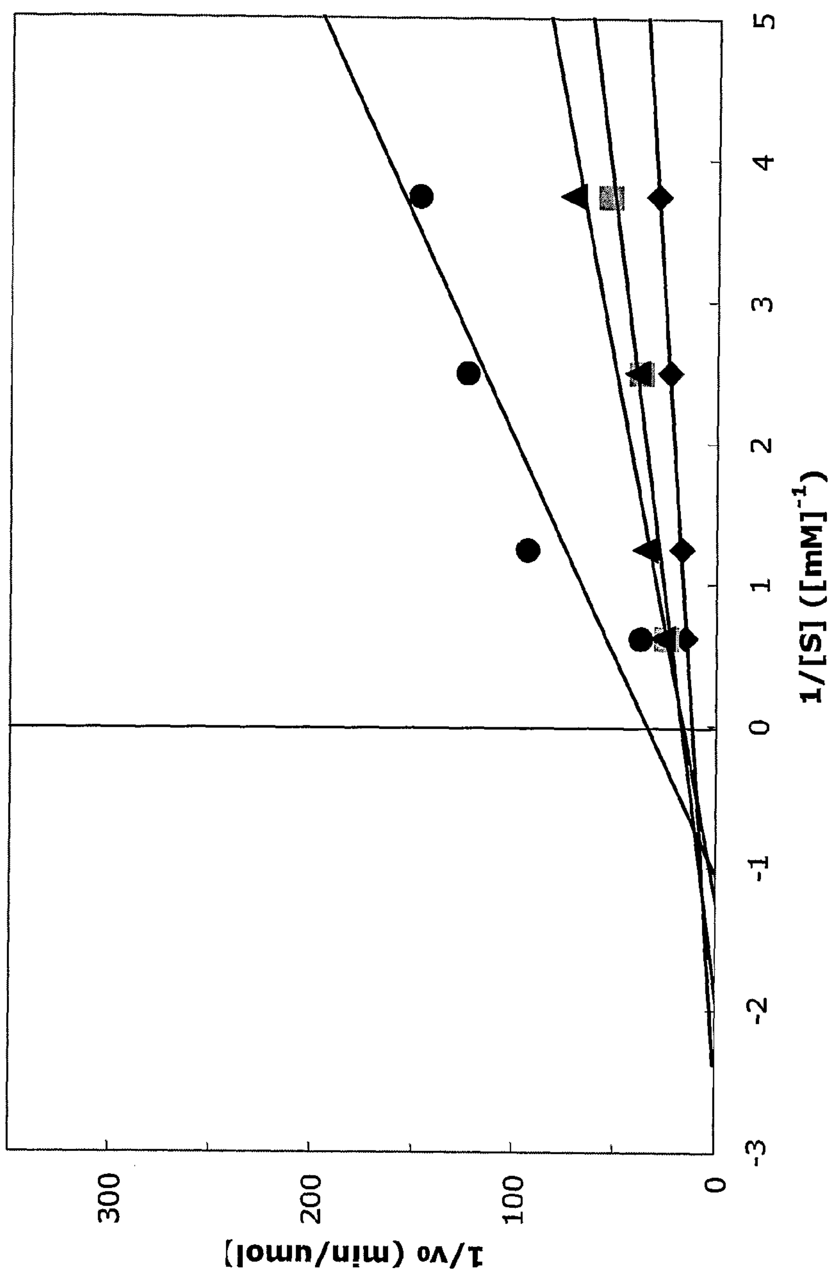
FIG. 9 shows a Lineweaver-Burk plot of inhibition of *B. cereus* 5/B/6 metallo-β-lactamase by the 30-mer RNA.
Figure 10:
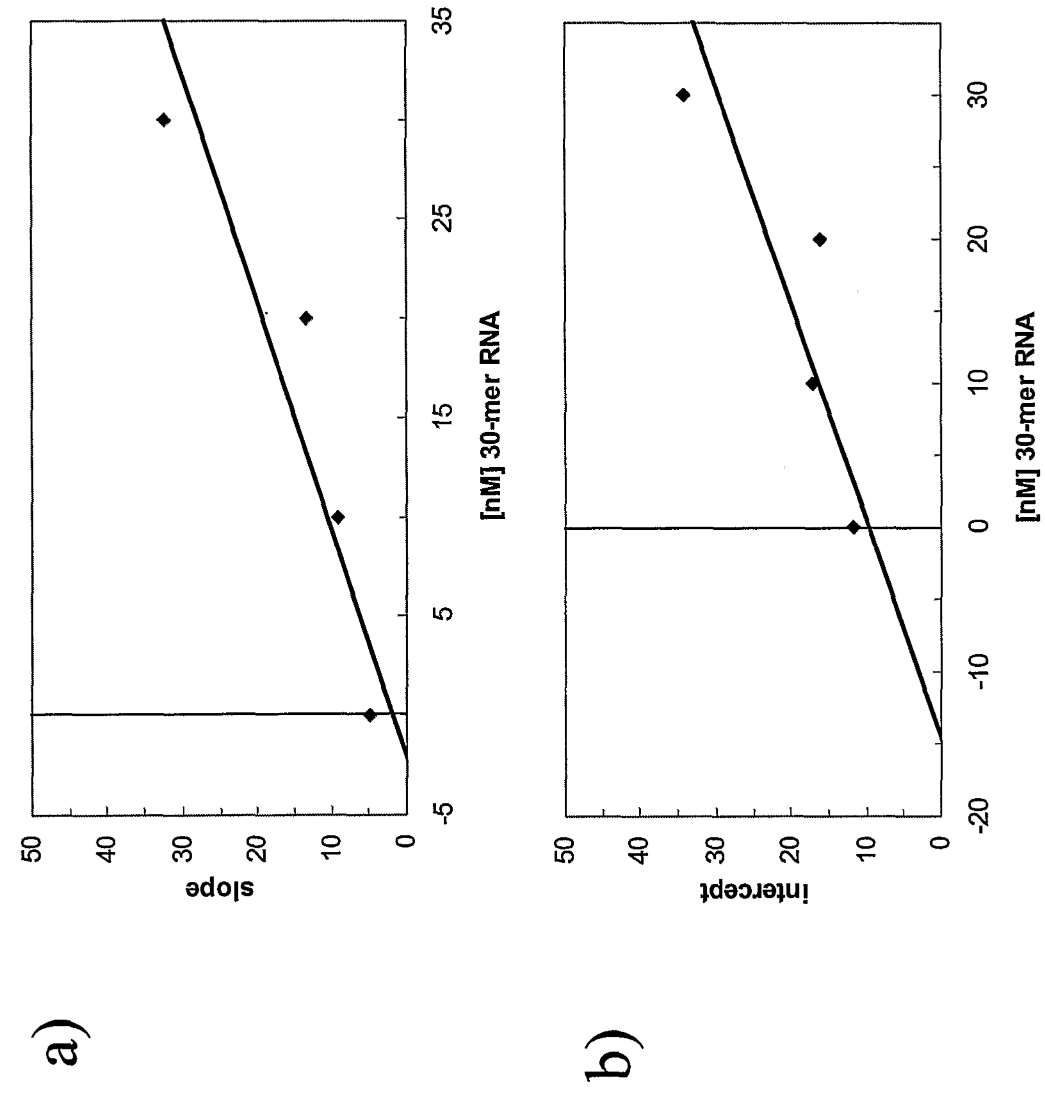
FIG. 10 shows slope and intercept replots to estimate $K_i$ and $K_i'$ for the 30-mer RNA.

From a steady-state kinetic study, the 30-mer showed a noncompetitive inhibition, as shown in FIG. 9. The value of $K_i$ (dissociation constant for the inhibitor from the enzyme-inhibitor complex) for the 30-mer was 2 nM and the value of $K_i'$ (dissociation constant for the inhibitor from the enzyme-substrate-inhibitor complex) for the 30-mer was 15 nM as determined by slope and intercept replots, as shown in FIG. 10.

Figure 8:
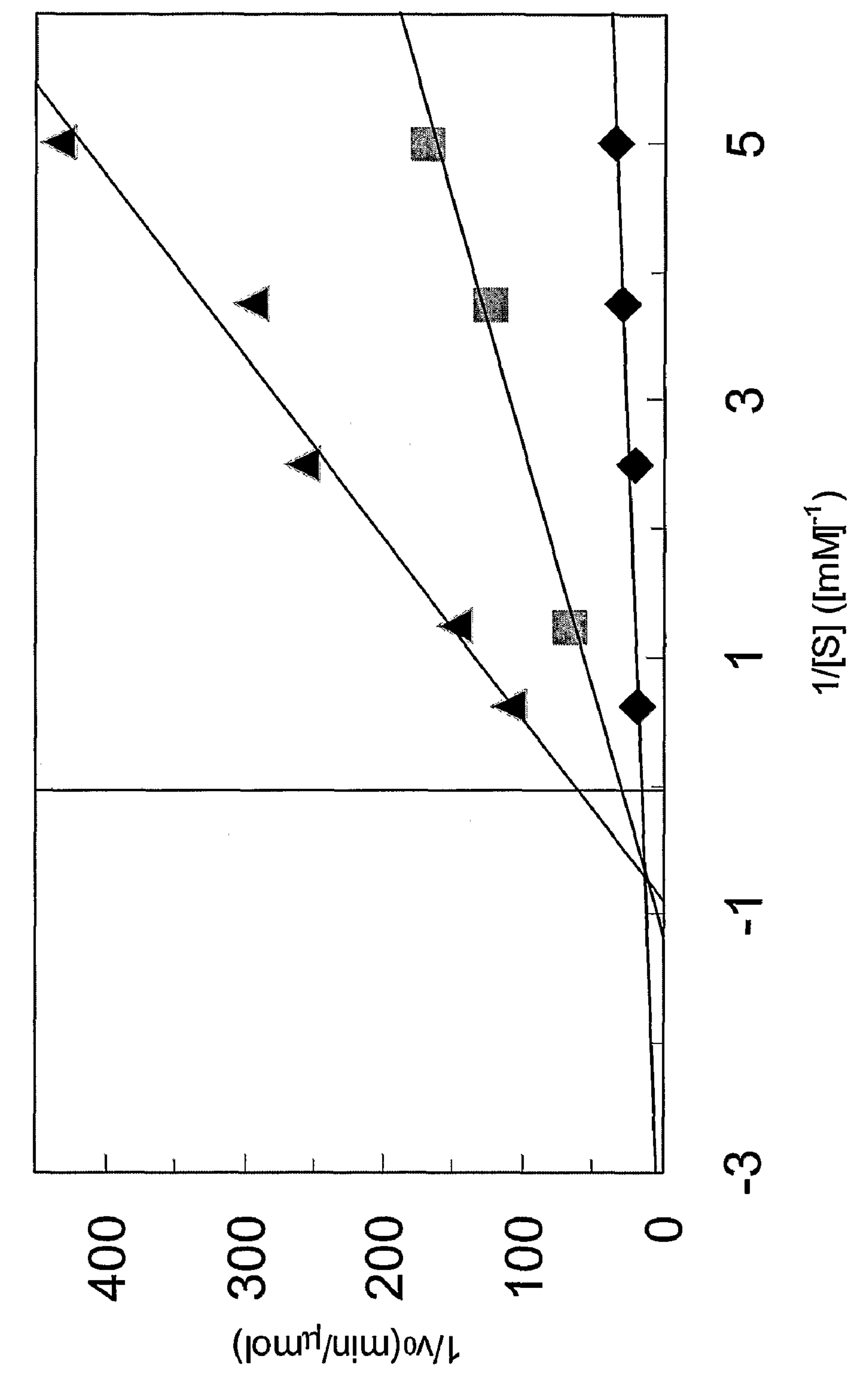
FIG. 8 shows a Lineweaver-Burk plot of inhibition of *B. cereus* 5/B/6 metallo-β-lactamase by EDTA.

A Lineweaver-Burk plot of the inhibition of *B. cereus* 5/B/6 metallo-β-lactamase by EDTA is shown in FIG. 8, wherein the Diamond: [I]=0 μM; square: [I]=3 μM; triangle: [I]=5 μM. I=EDTA.:

A Lineweaver-Burk plot of inhibition of *B. cereus* 5/B/6 metallo-β-lactamase by the 30-mer RNA is shown in FIG. 9, wherein the Diamond: [I]=0 nM; square: [I]=1 nM; triangle: [I]=2 nM; circle: [I]=3 nM. I=the 30-mer RNA.

As shown in FIG. 10A, a slope replot was used to estimate $K_i$ for the 30-mer RNA. Slope values ($K_m/V_{max}*(1+[I]/K_I)$) were plotted versus corresponding inhibitor concentrations. The x-intercept in this plot is $-K_i$. FIG. 10B shows the intercept replot to estimate $K_i'$ for the 10-mer. Intercept values ($1/V_{max}*(1+[I]/K_I)$) were plotted versus corresponding inhibitor concentrations. The x-intercept in this plot is $-K_i'$.

Figure 11:
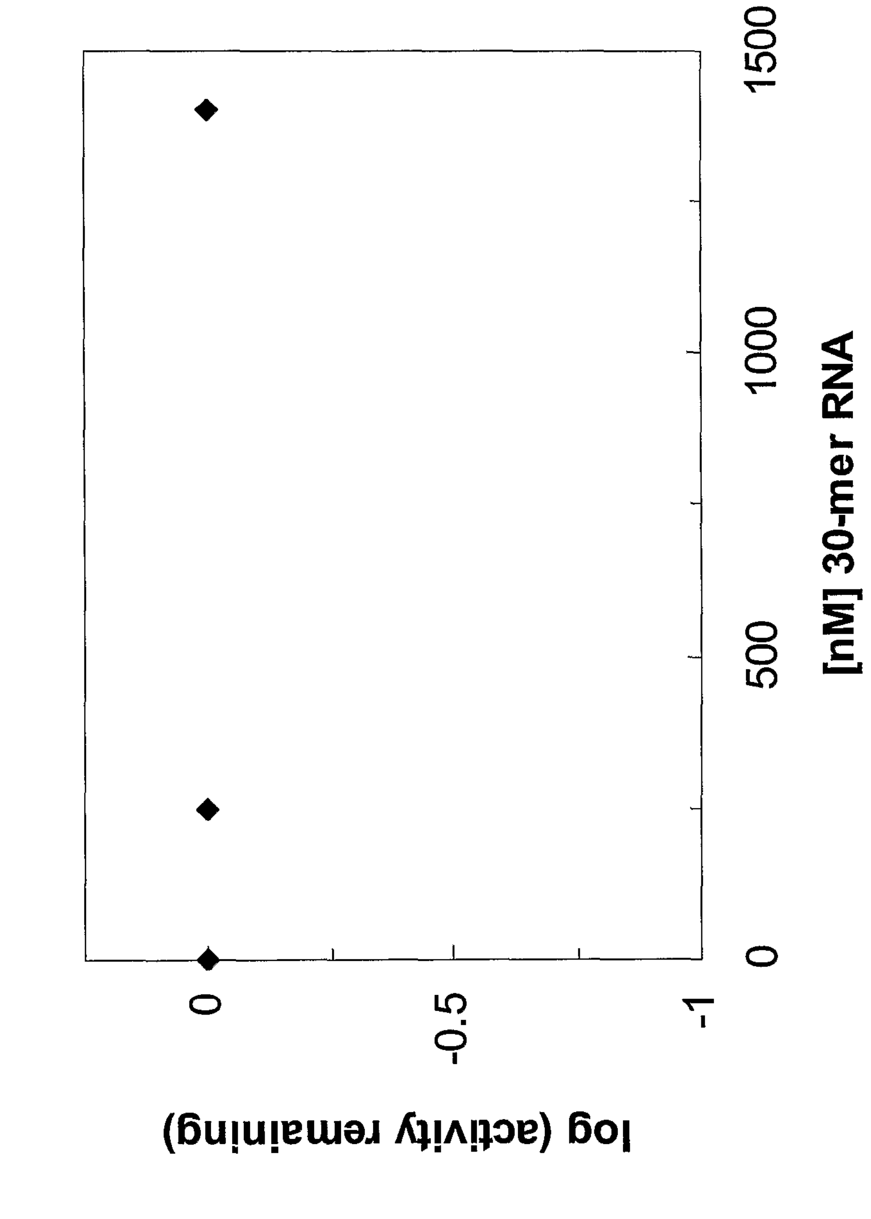
FIG. 11 shows an inhibition of *B. cereus* 569/H/9 β-lactamase I by various concentrations of the 30-mer RNA.

An experiment was performed to test the specificity of inhibition of the 30-mer (Seq ID No.:6). The inhibition of *B. cereus* 569/H/9 β-lactamase I (Seq ID No.:7) was tested using various concentrations of the 30-mer RNA. The concentration of the substrate (benzylpenicillin) was 1.1 mM in the buffer (50 mM MOPS (pH 7.0)/1 nM EDTA). As shown in FIG. 11, 250 nM of the 30-mer (23×$IC_{50}$ for the metallo-β-lactamase) has no effect on the activity of the *B. cereus* 569/H/9 β-lactamase I (a class A β-lactamase).

Figure 12:
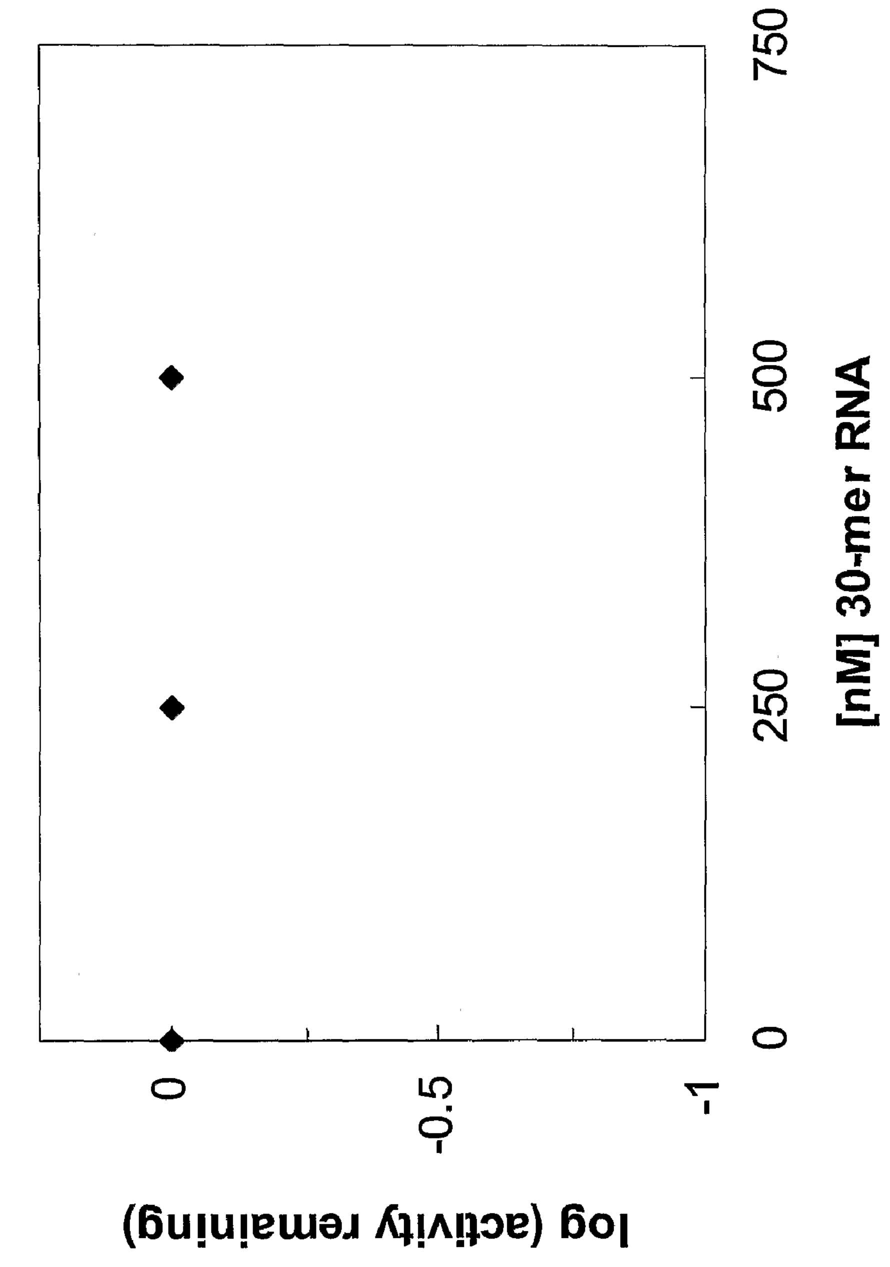
FIG. 12 shows an inhibition of bovine carboxypeptidase A by various concentrations of the 30-mer RNA.

In addition, the zinc dependent bovine carboxypeptidase A was used to test the specificity of inhibition by this 30-mer. The inhibition of bovine carboxypeptidase A was tested using various concentrations of the 30-mer RNA. The concentration of the substrate (hippuryl-L-phenylalanine) was 1 mM in the buffer (0.05 M Tris-HCl, pH 7.5, with 0.5 M sodium chloride). As shown in FIG. 12, 250 nM of the 30-mer (23× $IC_{50}$ for the metallo-β-lactamase) has no effect on the activity of the zinc-dependent carboxypeptidase A.

Figure 13:
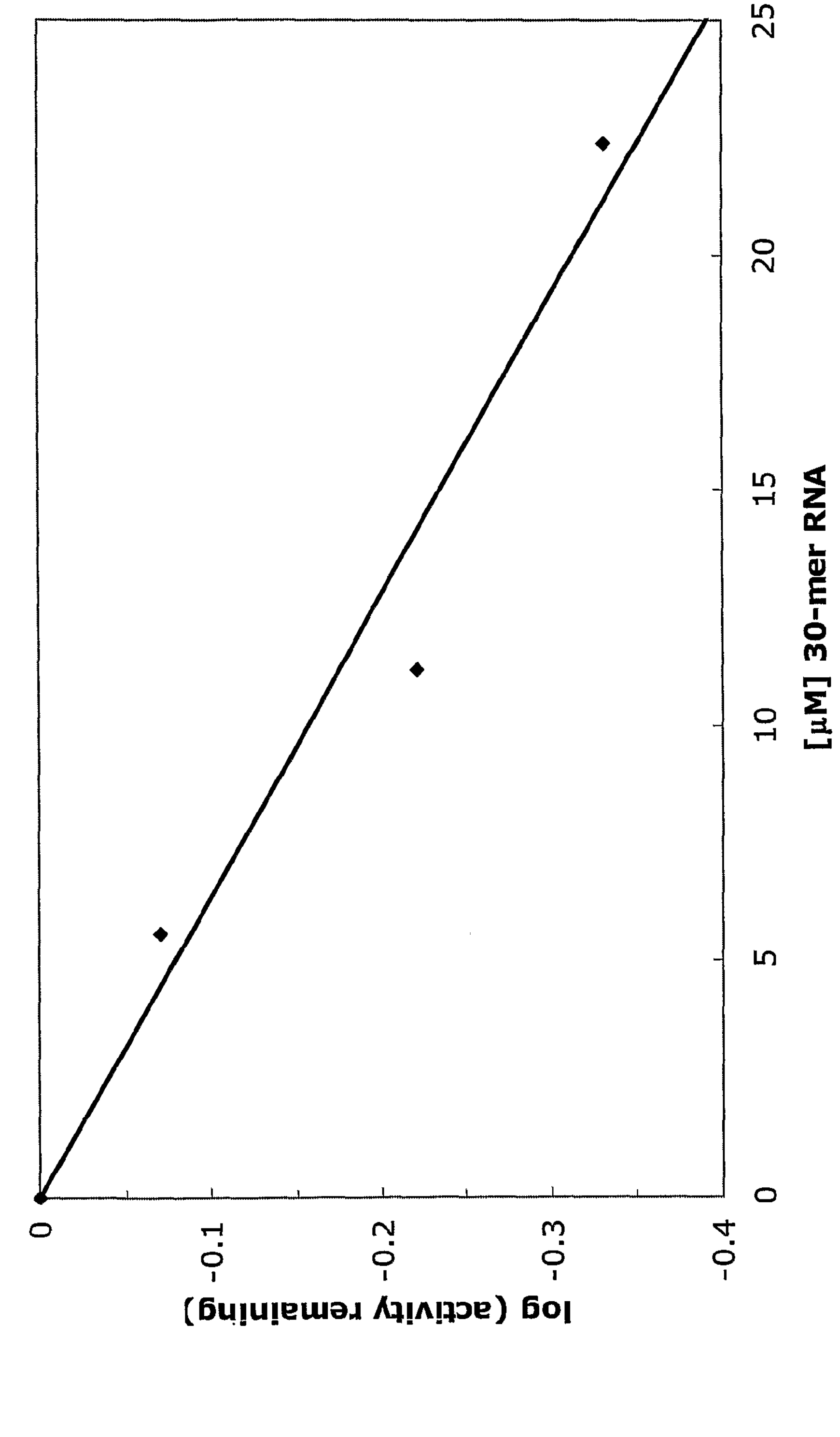
FIG. 13 shows a determination of $IC_{50}$ for *B. cereus* 5/B/6 metallo-β-lactamase in the presence of $Zn^{2+}$ ions by the 30-mer RNA.

As a control experiment, in order to check to see if the 30-mer binds to metal ion(s) in the active site of the metallo-β-lactamase, the assay for the metallo-β-lactamase was carried out in the presence of 1 mM $ZnSO_4$. The $IC_{50}$ value for the 30-mer was greatly elevated up to 19.3 μM because of the excess $Zn^{2+}$ ions. As shown in FIG. 13, the determination of $IC_{50}$ for *B. cereus* 5/B/6 metallo-β-lactamase in the presence of $Zn^{2+}$ ions by the 30-mer RNA. The concentration of the substrate (cephalosporin C) was 4.3 mM in the buffer (50 mM MOPS and 1 mM $ZnSO_4$, pH 7.0).

Figure 14:
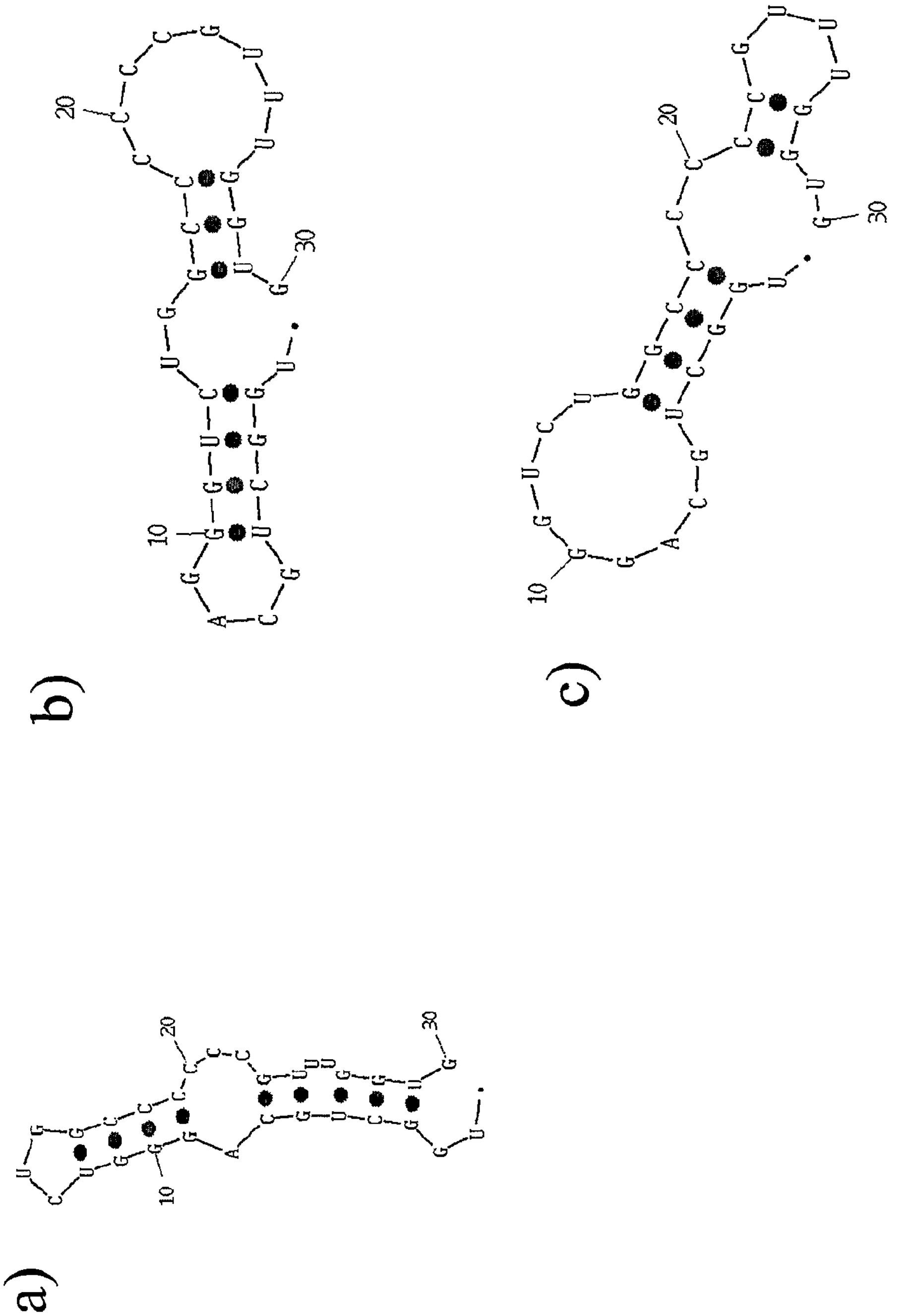
FIG. 14 shows predicted structures of the 30-mer RNA calculated by MFold program for SEQ ID NO. 5.
Figure 15:
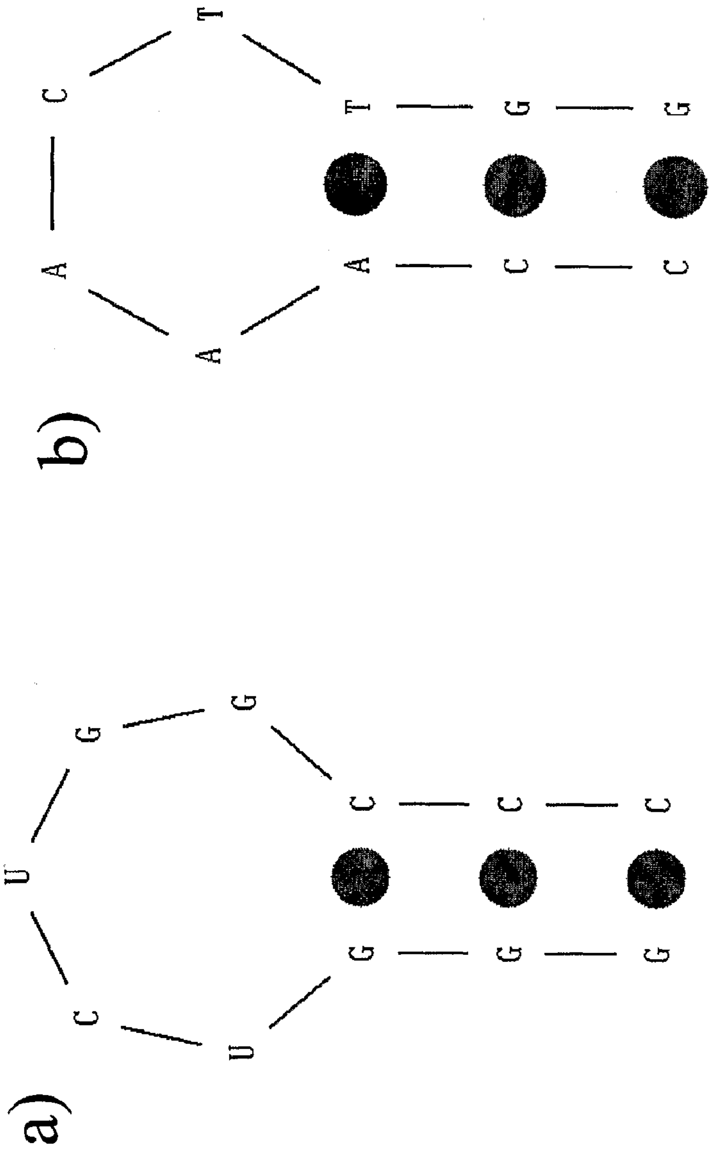
FIG. 15 shows a predicted secondary structure of 11-mer RNA for SEQ ID NO. 4.

11-mer RNA. As discussed above, MFold program (Zuker, 1989) calculated several possible structures for the 30-mer RNA, as shown in FIG. 14. Upon inspection of the various loops, the 11-mer loop from the first structure showed the closest homology to the 10-mer (Seq ID No 6) ssDNA inhibitor of metallo-β-lactamase, as shown in FIG. 15. This 11-mer RNA (5'-GGGUCUGGCCC-3') (Seq ID No.: 4) was synthesized and tested for inhibition.

Figure 16:
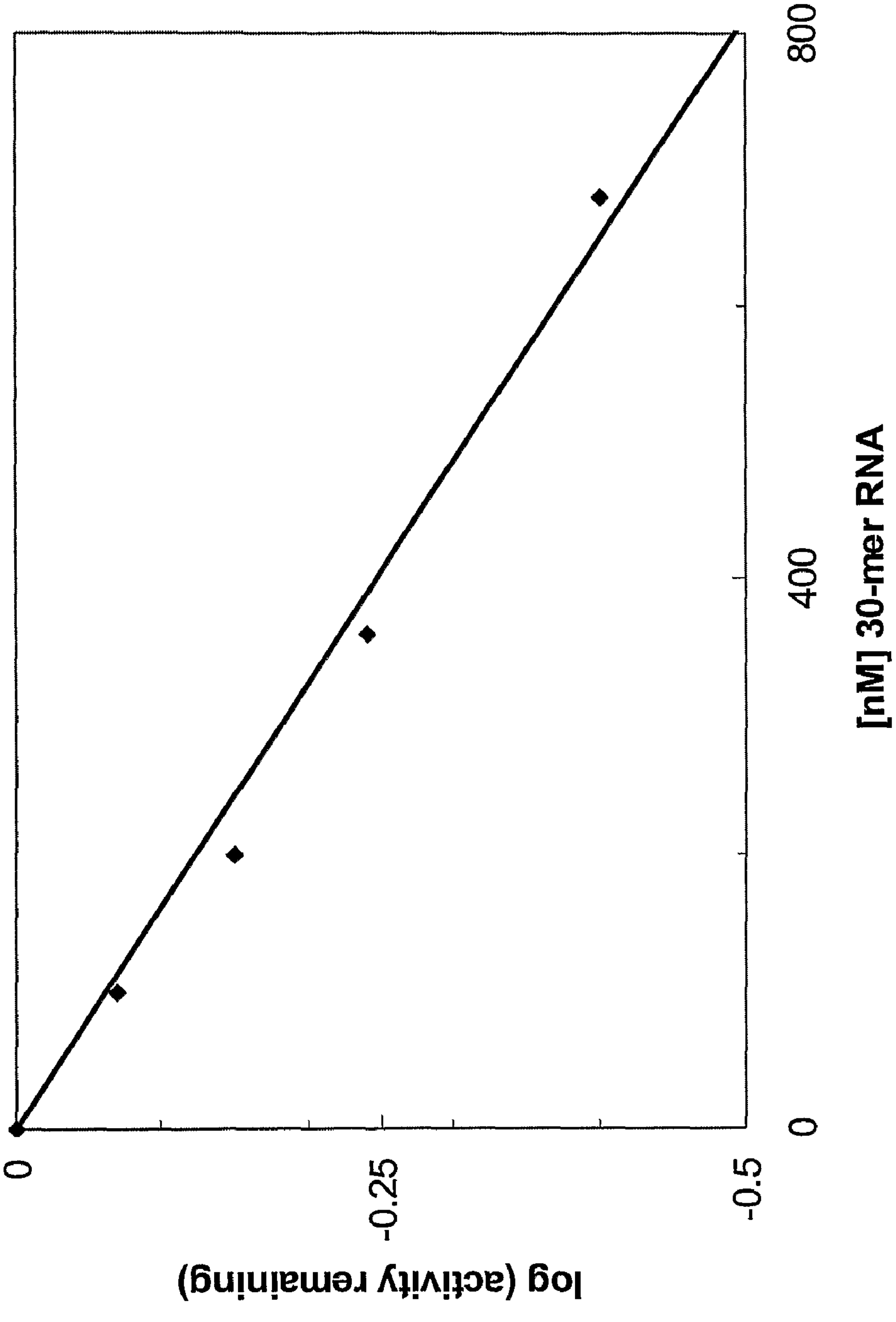
FIG. 16 shows determination of $IC_{50}$ for *B. cereus* 5/B/6 metallo-β-lactamase by the 11-mer RNA.

The $IC_{50}$ value for the 11-mer was determined by measuring the rate of enzymatic hydrolysis of cephalosporin C assayed in presence of different amounts of the 11-mer RNA. The determination of $IC_{50}$ for *B. cereus* 5/B/6 metallo-β-lactamase by the 11-mer RNA was carried out using a concentration of the substrate (cephalosporin C) of about 4.3 mM in the buffer (50 mM MOPS, pH 7.0). The $IC_{50}$ value for the 11-mer was 430 nM, as shown in FIG. 16.

Figure 17:
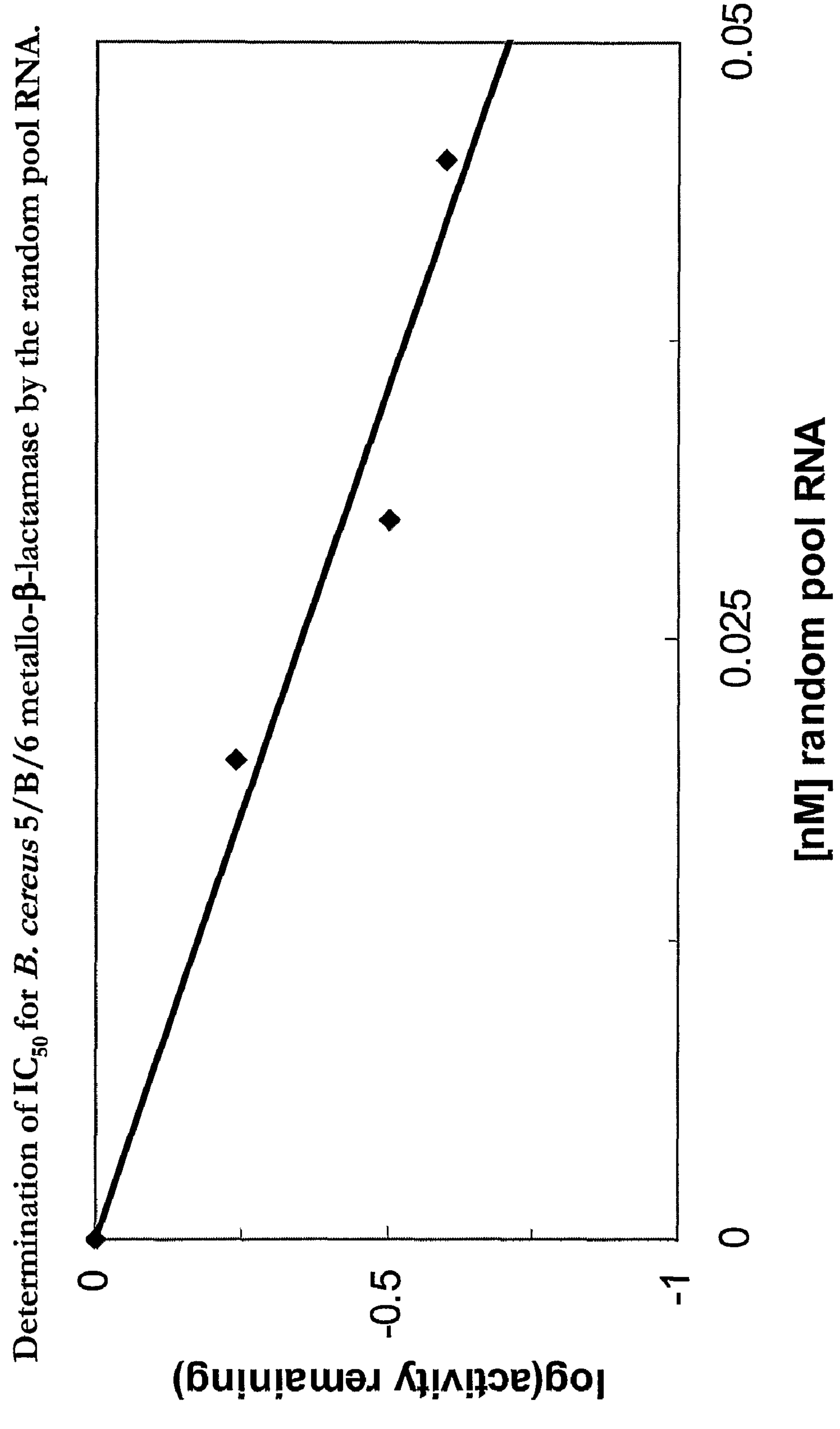
FIG. 17 shows determination of $IC_{50}$ for *B. cereus* 5/B/6 metallo-β-lactamase by the random pool RNA.

Random pool RNA. The $IC_{50}$ value for the random pool RNA was determined by measuring the rate of enzymatic hydrolysis of cephalosporin C assayed in presence of different amounts of the random pool RNA. The determination of $IC_{50}$ for *B. cereus* 5/B/6 metallo-β-lactamase by the random pool RNA was determined using the concentration of the substrate (cephalosporin C) of about 4.3 mM in the buffer (50 mM MOPS, pH 7.0). The $IC_{50}$ was determined to be 21 pM, as shown in FIG. 17.

Example 3

The SELEX methodology was utilized to generate high-affinity oligonucleotides that inhibit metallo-β-lactamase. By increasing the salt concentrations during the course of SELEX an increase in the stringency of selection was acheived, which helped to eliminate nonspecific-binding oligonucleotides and for the RNA experiments. Using this strategy, a single nucleic acid sequence was found after twelve rounds of SELEX. Although not wanting to be bound by theory, the inhibitor data indicate that that the 30-mer RNA may be noncompetitive inhibitor similar to EDTA. The $IC_{50}$ value for the 30-mer RNA in the presence of excess $Zn^{2+}$ was greatly elevated compared to the assay with no $Zn^{2+}$ present, although not wanting to be bound by theory, such data may suggest that the 30-mer RNA may bind the metal ion(s). Similar to the chelation of metal ions to EDTA, the 30-mer RNA may bind to one or more $Zn^{2+}$ ions in the active site of the enzyme. Several crystal structures of metallo-β-lactamase in complex with inhibitors are available (Garcia-Saez, I., et. al., 2003; Fitzgerald, P. M. et. al., 1998; Concha, N. O. et. al., 2000; Toney, J. H. et. al., 2001); all characterized inhibitors are able to bind to the active-site metal ions.

A 10-mer ssDNA was identified as an efficient inhibitor of the enzyme in the international patent application WO 2004/031142 A2 entitled "Inhibition of Metalo-Beta-Lactamase" published on Apr. 15, 2004 with Shaw et al., listed as inventors. One aspect of the current invention used SELEX to identify a 30 mer RNA-based inhibitor of a metallo-β-lactamase. Although not wanting to be bound by theory, the 30-mer RNA inhibitor and the 10-mer ssDNA both show inhibition in the nanomolar range, as shown in FIG. 18.

An assay for the 30-mer RNA with β-lactamase I was conducted to determine whether or not the 30-mer RNA competed for the substrate-binding site of the enzyme. Generally, the 30-mer RNA has no effect on the activity of β-lactamase I. This is consistent with the noncompetitive inhibition pattern discussed previously and further demonstrates the selective nature of the 30-mer RNA for metallo-β-lactamase.

Bovine carboxypeptidase A is a metal-dependent enzyme which has been compared to the metallo-β-lactamase as a model in terms of structural and mechanistic features (Alberts et al., 1998: Bouagu et al., 1998). The lack of inhibition for carboxypeptidase A in the presence of 30-mer RNA that is more than $23\times IC_{50}$ for the metallo-β-lactamase shows the exquisite specificity for the metal ion of metallo-β-lactamase. Unlike EDTA or other metal chelators, it has been shown that the 30-mer RNA does not indiscriminately chelate all zinc sources even though the kinetic data suggest metal coordination by the 30-mer RNA. Although not wanting to be bound by theory, the inhibition by the 30-mer RNA is very specific to metallo-β-lactamase.

Generally, both oligomers (e.g. 30-mer RNA and 10-mer ssDNA) have $IC_{50}$'s in the nanomolar range and have a specificity for metallo-β-lactamase, wherein the oligomers do not show inhibition for β-lactamase I nor carboxypeptidase A, as shown in FIG. 19.

The MFold program predicted an 11-mer loop in the 30-mer structure that shares some homology to the 10-mer ssDNA. Both are of short length containing a duplex GC-stem region and the oligonucleotides comprising the loops are of similar bases. Comparing the loop structures of the 10-mer ssDNA and the 11-mer RNA, both have two purine bases followed by two to three pyrimidine bases, as shown in FIG. 17. These similarities suggest that the stem or the loop region may be important for the inhibition of the enzyme. By comparing the $IC_{50}$ values of the 30-mer RNA and the 11-mer RNA, much inhibition is lost upon shortening the oligonucleotide. Although not wanting to be bound by theory, modifications can be made by either shortening the stem region of the loop or changing the nucleotides within the stem and/or the loop. The 11-mer is an effective inhibitor in the nanomolar range and upon modifications of both the 30-mer and 11-mer RNAs, any increase in inhibition of metallo-β-lactamase can be tested. Another aspect of the current invention suggests that other possible loop structures formed from the predicted secondary structures of the 30-mer RNA can be utilized as inhibitors. Likewise, these structures can also be shortened and modified for inhibition.

Currently, there are several aptamers which are in clinical trials as inhibitors and the first modified-oligonucleotide drug has achieved marketing clearance. AGRO100, a G-rich oligonucleotide, is in clinical trials as an anti-cancer drug for the treatment of solid tumors (Aptamera, 2004); AGRO100 represents a potentially powerful example of "molecularly targeted" cancer drugs. Macugen is currently being studied for treatment of age-related macular degeneration and diabetic macular edema (Eyetech Pharmaceuticals, 2004). Macugen is an aptamer that is attached to a molecule of polyethylene glycol (PEG); this PEGylation increases the half-life of the product, which in turn increases the time that Macugen is available in the eye. Vitravene is a 21-nucleotide phosphoromonothioate antisense drug that is used to treat a condition called cytomegalovirus retinitis in people with AIDS (Novartis Ophthalmics, 2004). Vitravene demonstrates the effectiveness of an aptamer drug in the treatment of local disease; it demonstrates that an aptamer drug can be federally approved and can be manufactured for commercial use.

So far what is known about these aptamers in clinical trials are that, in general, they tend not to trigger adverse immune responses. This is advantageous as aptamers combine the optimal characteristics of high specificity and affinity, biological and chemical stability, and yet, they are effective drugs at low toxicity. In contrast to other therapeutic approaches, such as monoclonal antibodies, aptamers are chemically synthesized rather than biologically expressed, offering a significant cost advantage. Although not wanting to be bound by theory, aptamers could potentially be used in a wide range of disease areas including bacterial infectious diseases.

The 11-mer and 30-mer RNAs and the 10-mer DNA are among the most effective inhibitors of metallo-β-lactamase. Other known inhibitors of metallo-β-lactamases that have been identified have $IC_{50}$ values in the micromolar range (Garcia-Saez, I., et. al., 2003; Payne et al., 1997; Yang and Crowder, 1999; Scrofani et al., 1999); one exception is a tricyclic natural product with an $IC_{50}$ value of 300 nM (Payne et al., 2002). For a preliminary study, the random RNA pool before the first SELEX round was tested for inhibition of metallo-β-lactamase. The random RNA pool exhibited strong inhibition estimated to be in the picomolar range. Although not wanting to be bound by theory, this suggests the possibility of a more effective inhibitor present in the pool that was not selected or possibly that the inhibition is due to a combination of inhibitors. In the future, another SELEX experiment will be conducted with the random pool to determine the presence of more efficient RNA inhibitors.

The compositions and methods described herein are by no means all-inclusive, and further methods to suit the specific application will be apparent to the ordinary skilled artisan. The scope of the ligands covered by this invention extends to all nucleic acid ligands of lactamase and metallo-lactamases. Moreover, the effective amount of the compositions can be further approximated through analogy to compounds known to exert the desired effect.

REFERENCES CITED

The following references, to the extent that they provide exemplary procedural or other details supplementary to those set forth herein, are specifically incorporated herein by reference.

Patent Documents

WO 2004/031142 A2 entitled "Inhibition of Metallo-Beta-Lactamase" published on Apr. 15, 2004 with Shaw et al., listed as inventors.

U.S. Pat. No. 5,637,459 entitled "Systematic Evolution of Ligands by Exponential Enrichment: Chimeric Selex" issued on Jun. 30, 1998 with Burke et al., listed as inventors.

U.S. Pat. No. 5,773,598 entitled "Systematic Evolution of Ligands by Exponential Enrichment: Chimeric Selex" issued on Jun. 30, 1998 with Burke et al., listed as inventors.

REFERENCES CITED

Abraham, E. P. and Waley, S. G. (1979) in *Beta-Lactamases* (Hamilton-Miller, J. M. T. and Smith, J. T., eds.) pp. 311-338, Academic Press, New York.

Alberts, I. L., Katalin, N. and Wodak, S. J. (1998) Analysis of Zinc Binding Sites in Protein Crystal Structures. *Protein Science* 7, 1700-1716.

Ambler, R. P. (1980) The Structure of ®-lactamases. *Phil. Trans. R. Soc. Lond.* B289, 321-331.

Ambler, R. P., Coulson, A. F. W., Frere, J.-M., Ghuysen, J.-M., Joris, B., Forsman, M., Levesque, R. C., Triaby, G. and Waley, S. G. (1991) A Standard Numbering Scheme for the Class A ®-lactamases. *Biochem. J.* 276, 269-270.

Aptamera (2004). *Lead Anti-Cancer Drug Compound-AGRO* 100. Retrieved on Sep. 22, 2004 on the World Wide Web: http://www.aptamera.com/aptamera_leaddrugcandidate.pdf Bartel, D. and Szostak, J. (1993) Isolation of New Ribozymes from a Large Pool of Random Sequences. *Science.* 261, 1411-1418.

Bassett, S. E., Fennewald, S. M., King, D. J., Xin L., Norbert K. H., Shope, R., Aronson, J. F., Luxon, B. A., and Gorenstein., D. G. (2004) Combinatorial Selection and Edited Combinatorial Selection of Phosphorothioate Aptamers Targeting Human Nuclear Factor-β RelA/p50 and RelA/RelA. *Biochemistry.* 43, 9105-9115.

Bicknell, R., Schaffer, A., Waley, S. G., Auld, D. S. (1986) Changes in the Coordination Geometry of the Active-Site Metal during Catalysis of Benzylpenicillin Hydrolysis by *Bacillus cereus* β-Lactamase II. *Biochemistry.* 25, 7208-7215.

Bouagu, S., Laws, A., Galleni, M. and Page, M. (1998) The Mechanism of Catalysis and the Inhibition of the *Bacillus cereus* Zinc-Dependent ®-lactamase *Biochem. J.* 331, 703-711.

Brenner, D. G. and Knowles, J. D. (1984) Penicillanic Acid Sulfone: Nature of Irreversible Inactivation of RTEM ®-Lactamase from *Escherichia coli. Biochemistry* 23, 5834-5846.

Brown, T. A. (1998) Klenow Fragment. *Molecular Biology Labfax,* $2^{nd}$ ed. 1, 147-148

Carfi, A., Pares, S., Duee, E., Galleni, M., Duez, C., Frere, J. M. and Dideberg, O. (1995) The 3-D Structure of a Zinc Metallo-β-Lactamase from *Bacillus cereus* Reveals a New Type of Protein Fold. *The EMBO Journal,* 14, No. 20, 4914-4921.

Concha, N. O., Janson, C. A., Rowling, P., Pearson, S., Cheever, C. A., Clarke, B. P., Lewis, C., Galleni, M., Fere, J. M., Payne, D. J., Bateson, J. H., and Abdel-Meguid, S. S. (2000) Crystal Structure of the IMP-1 Metallo-®-Lactamase from *Pseudoinonas aeruginosa* and Its Complex with a Mercaptocarboxylate Inhibitor: Binding Determinants of a Potent, Broad-Spectrum Inhibitor. *Biochemistry* 39, 4288-4298.

Concha, N. O., Rasmussen, B. A., Bush, K. and Herzberg, O. (1996) Crystal Structure of the Wide-Spectrum Binuclear Zinc ®-lactamase from *Bacteroides fragilis. Structure* 4, 823-836.

Crompton, B., Jago, M., and Abraham, E. P. (1962) Behavior of Some Derivatives of 7-Aminocephalosponaic Acid and 6-aminopenicillanic Acid as Substrates, Inhibitors, and Inducers of Penicillinases. *Biochem. J.* 83, 52-63.

Danziger, L. H. and Pendland, S. L. (1995) Bacterial Resistance of ®-lactam Antibiotics. Am. J. health Syst. Pharm. 52 (Suppl 2), S3-8.

Davies, R., and Abraham, E. (1974) Comparison of β-lactamase II from *Bacillus cereus* 569/H/9 with a ®-lactamase from *Bacillus cereus* 5/B/6. *Biochem. J.* 145, 409-411.

Davies, R., and Abraham, E. (1974) Metal Cofactor Requirements of ®-lactamase II. *Biochem. J.* 143, 129-135.

Davies, R., and Abraham, E. (1974) Separation Purification and Properties of ®-lactamase I and β-lactamase II from *Bacillus cereus* 569/H/9. *Biochem. J.* 143, 115-127.

Eyetech Pharmaceuticals (2004) Macugen™-Basics. Retrieved on Sep. 22, 2004 on the World Wide Web: http://www.eyetk.com/science/science_vegf.asp Felici, A., Amicosante, G. (1993) An Overview of the Kinetic Parameters of Class B ®-lactamases. *Biochem. J.* 291, 151-155.

Fisher, J., Charnas, R. L, Bradley, S. M. and Knowles, J. R. (1981) Inactivation of the RTEM ®-lactamase from Escherichia coli. Interaction of Penam Sulfones with *Enzyme. Biochemistry* 20, 2726-2731.

Fitzerald, P. M., Wu, J. K., and Toney, J. H. (1998) Unanticipated Inhibition of the Metallo-β-lactamase from *Bacteroides fragilis* by 4-Morpholineethanesulfonic Acid (MES): A Crystallographic Study at 1.85-Å Resolution. *Biochemistry.* 37, 6791-6800.

Folk, J. E. and Schirmer, E. W. (1963) The Porcine Pancreatic Carboxypeptidase A System. J. Biol. Chem. 238, 3884-3894.

Freier, S. M., Kierzek, R., Jaeger, J. A., Sugimoto, N., Caruthers, M. H., Neilson, T., and Turner, D. H. (1986). Improved Free-Energy Parameters for Predictions of RNA Duplex Stability. *Proc. Natl. Acad. Sci.* 83, 9373-9377.

Frere, J. M. (1995) Beta-Lactamases and Bacterial Resistance to Antibiotics. *Mol. Microbiol.* 16 (3), 385-395.

Garcia-Saez, I., Hopkins, J., Papamicael, C., Franceschini, N., Amicosante, G., Rossolini, G. M., Galleni, M., Frere, J. M., and Dideberg, O. (2003) The 1.5-Å Structure of *Chryseobacterium meningosepticum* Zinc ®-Lactamase in Complex with the Inhibitor, D-Captopril. *J. Biol. Chem.* 278, 23868-23873.

Ghuysen, J.-M. (1988) in Antibiotic Inhibition of Bacterial Cell Surface Assembly and Function (Actor, P., Daneo-Moore, L., Higgins, M. L., Salton, M. R. J. and Shockman, G. D., Ed.) pp. 268-284, American Society for Microbiology, Washington, D. C.

Gold, L., Polisky, B., Uhlenbeck, O. and Yarus, M., (1995) Diversity of Oligonucleotide Functions. *Annu. Rev. Biochem.* 64, 763-797.

Hanahan, D. (1983) Studies on Transformation of *Escherichia coli* with Plasmids. *J. Mol. Biol.* 166, 557-580

Hussain, M., Pastor, F. I, Lampen, J. O. (1987) Cloning and Sequencing of the blaZ Gene Encoding ®-lactamase II, a Lipoprotein of *Bacillus cereus* 569/H. *J. Bacteriology* 169, 579-585.

Jaeger, J. A., Turner, D. H., and Zuker, M. (1989) Improved Predictions of Secondary Structures for RNA. *Proc. Natl. Acad. Sci.* 86, 7706-7710.

Jaeger, J. A., Turner, D. H., and Zuker, M. (1990) Predicting Optimal and Suboptimal Secondary Structure for RNA. *Methods in Enzymology.* 183, 281-306.

Joris, B., Ledent, P., Dideberg, O., Fonze, E., Lamotte-Brasseur, J., Kelly, J. A., Ghuysen, J.-M. and Frere, J.-M. (1991) Comparison of the Sequences of Class A ®-Lactamases and of the Secondary Structure Elements of Penicillin-Recognizing Proteins. Antimicrob. Agents Chemother. 35, 2294-2301.

Kelly, J. A., Knox, J. R., Moews, P. C., Moring, J. and Zhao, H. C. (1988) in *Antibiotic* Inhibition of Bactrial Cell surface Assembly and Function (Actor, P., Daneo Moore, L., Higgins, M. L., Salton, M. R. J. and Shockman, G. D., Ed.) pp. 261-267, American Society for Micro biology, Washington, D.C.

Kim, S. K. (2002) Inhibition of Metallo-®-lactamase by Rational and Combinatorial Approaches. Ph.D. thesis, Texas Tech University Klug, S. J., and Famulok, M. (1994) All You Wanted to Know About SELEX. *Molecular Biology Reports* 20, 97-107.

Kuwabara, S. and Lloyd, P. (1971) Protein and Carbohydrate Moieties of a Preparation of β-lactamase II. *Biochem. J.* 124, 215-220.

Ledent, P., Raquet, X., Joris, B., and Frere, J. (1993) A Comparative Study of class D ®-lactamases. *Biochem. J.* 292, 555-565.

Lim, H. M., Pene, J. J., and Shaw, R. W. (1988) Cloning, Nucleotide Sequence, and Expression of the *Bacillus cereus* 5/B/6 ®-Lactamase II Structural Gene. *J. Bacteriology.* 170, 2873-2878.

Livermore, D. M. (1991) Mechanisms of Resistance to ®-Lactam Antibiotics. *Scand. J. Infect. Dis., Suppl.* 78, 7-16.

Lowery, O. H., Rosenberg, N. J., Farr, A. L., and Randall, R. J. (1951) Protein Measurement with the Folin Phenol Reagent. *J. Biol. Clem.* 193, 265-275.

Maugh, T. M. (1981) A New Wave of Antibiotics Builds. *Science* 214, 1225-1228.

Maxam, A. M. and Gilbert, W. (1977) A new method for sequencing DNA. *Proc. Natl. Acad. Sci. USA* 74, 560-564.

Meyers, J. L. and Shaw, R. W. (1989) Production, Purification and Spectral Properties of Metal-Dependent ®-Lactamases of *Bacillus cereus. Biochimica et Biophysica Acta.* 995, 264-272.

Mollard, C., Moali, C., Papamicael, C., Damblon, C., Vessilier, S., Amicosante, G., Schofield, C. J., Galleni, M., Frere, J. M. and Roberts, G. C. (2001) Thiomandelic Acid, a Broad Spectrum Inhibitor of Zinc ®-Lactamases. *J. Biol. Chem.* 276, 45015-45023.

Neu, H. (1992) The Crisis in Antibiotic Resistance. *Science.* 257, 1064-1093.

Novartis Ophthalmics (2004) Vitravene. Retrieved on Sep. 22, 2004 on the World Wide Web: http://www.isispharm.com/vitravene-P.html Payne, D. J., Bateson, J. H., Gasson, B. C., Proctor, D., Khushi, T, Farmer, T. H., Tolson, D. A., Bell, D., Skett, P. W., Marshall, A. C., Reid, R., Ghosez, L., Combret, Y. and Marchand-Brynaert, J. (1997) Inhibition of Metallo-®-Lactamases by a Series of Mercaptoacetic Acid Thiol Ester Derivatives. *Antimicrob. Agents Chemother.* 41, 135-140.

Payne, D. J., Hueso-Rodriguez, J. A., Boyd, H., and Concha, N. (2002) Identification of a Series of Tricyclic Natural Products as Potent Broad-Spectrum Inhibitors of Metallo-®-Lactamases. *Antimicrob. Agents Chemother.* 46, 1880-1886.

Pitout, J. D. D., Sanders, C. C. and Sanders, W. E. (1997) Antimicrobial Resistance with Focus on ®-Lactam Resistance in Gram-Negative Bacilli. *Am. J. Med.* 103, 51-59.

Rahil, J. and Pratt, R. F. (1991) Phosphonate monoester inhibitors of class A β-Lactamases. *Biochem. J.* 275, 793-795.

Rasmussen, B., Yang, Y., and Bush, K. (1994) Contribution of Enzymatic Properties, Cell Permeability, and Enzyme Expression to Microbiological Activities of β-Lactams in Three *Bacteroides fragilis* Isolates that Harbor a Metallo-β-lactamase Gene. *Antimicrobial Agents and Chemotherapy.* 38, 2116-2120.

Reddy, P., Peterkofsky, A. and McKenney, K. (1989) Hyperexpression and Purification of *Escherichia coli* Adenylate Cyclase Using a Vector Designed Expression of Lethal Gene Products. *Nucleic Acids Res.* 17, 10473-10488.

Robertson, D. and Joyce, G. (1990) Selection in vitro of an RNA Enzyme that Specifically Cleaves Single-Stranded DNA. *Nature.* 344, 467-468.

Sambrook, J., Fritsch, E. F. and Maniatis, T. (1989) *Molecular Cloning: A Laboratory Manual,* 2ed, pp. 7.70-7.76, Cold Spring Harbor Laboratory Press, New York.

Scrofani, S. D., Chung, J., Huntley, J. J., Benkovic, S. J., Wright, P. E. and Dyson, H. J. (1999) NMR Characterization of the Metallo-®-lactamase of *Bacteroides fragilis* and Its Interaction with a Tight-Binding Inhibitor: Role of an Active-Site Loop Biochemistry 44, 14507-14514.

Seeman, N. C., Rosenberg, J. M., and Rich, A. (1976) Sequence-Specific Recognition of Double Helical Nucleic Acids by Proteins. *Proc. Nat. Acad. Sci.* 73, 804-808.

Shaw, R. W., Clark, S. D., Hilliard, N. P. and Harman, J. G. (1991) Hyperexpression in *Escherichia coli*, Purification, and Characterization of the Metallo-®-lactamase of *Bacillus cereus* 5/B/6. *Prot. Exp. Purif* 2, 151-157.

Suskovic, B., Vajyner, Z., Naumski., R. (1991) Synthesis and Biological Activities of Some Peptidoglycan Monomer Derivatives. *Tetrahedron.* 47, 8407-8416.

Sutton, B. J., Artymiuk, P. J. and Waley, S. G. (1987) X-ray Crystallographic Study of β-Lactamase II from *Bacillus cereus* at 0.35 nm Resolution. *Biochem. J.* 248, 181-188.

Thatcher, D. (1975) The Partial Amino Acid Sequence of the Extracellular β-lactamase I of *Bacillus cereus* 569/H. 147, 313-326.

Toney, J. H., Hammond, G. G., Fitzgerald, P. M., Sharma, N., Balkovec, J. M., Rouen, G. P., Olson, S. H., Hammond, M. L., Greenlee, M. L., and Gao, Y. D. (2001) Succinic Acids as Potent Inhibitors of Plasmid-borne IMP-1 Metallo-®-lactamase. *J. Biol. Chem.* 276, 31913-31918.

Tuerk, C. and Gold, L. (1990) Systematic Evolution of Ligands by Exponential Enrichment: RNA Ligands to Bacteriophage T4 DNA Polymerase. *Science.* 249, 505-510.

Turner, D. H. and Sugimoto, N. (1988) RNA Structure Prediction. *Ann. Rev. Biophys. Biophys. Chem.* 17, 167-192.

Yang, K. W. and Crowder, M. W. (1999) Inhibition Studies on the Metallo-®-lactamase L1 from Stenotrophomonas maltophilia. Arch. Biochem. Biophys. 368, 1-6.

Zuker, M. (1989) On Finding All Suboptimal Foldings of an RNA Molecule. *Science.* 244, 48-52.

What is claimed is:

1. An isolated polyribonucleotide comprising a sequence that binds to a Class B metallo-β-lactamase, wherein the isolated polyribonucleotide is SEQ ID NO. 5.

2. A method of inhibiting the growth of Class B metallo-β-lactamase producing bacteria comprising:

Contacting the bacteria with at least:

(a) a β-lactam antibiotic; and (b) an isolated polyribonucleotide that is SEQ ID NO. 5 that binds to a class B metallo-β-lactamase.

3. The method of claim 2, wherein the β-lactam antibiotic is a penicillin.

4. The method of claim 2, wherein the β-lactam antibiotic comprises a cephalosporin.

* * * * *